United States Patent
Wardell et al.

(10) Patent No.: US 10,024,817 B2
(45) Date of Patent: Jul. 17, 2018

(54) METHOD FOR DETECTING PROTEASES AND ACTIVE INFECTION IN BIOLOGICAL FLUIDS AND TISSUES

(71) Applicants: Mark R. Wardell, Fort Myers, FL (US); Kenneth A. Sabacinski, Plantation, FL (US)

(72) Inventors: Mark R. Wardell, Fort Myers, FL (US); Kenneth A. Sabacinski, Plantation, FL (US)

(73) Assignee: PeloGenix, LLC, Fort Myers, FL (US)

( * ) Notice: Subject to any disclaimer, the term of this patent is extended or adjusted under 35 U.S.C. 154(b) by 463 days.

(21) Appl. No.: 14/887,291

(22) Filed: Oct. 19, 2015

(65) Prior Publication Data
US 2016/0109401 A1    Apr. 21, 2016

Related U.S. Application Data

(60) Provisional application No. 62/065,440, filed on Oct. 17, 2014.

(51) Int. Cl.
*G01N 27/327* (2006.01)
*G01N 33/543* (2006.01)
*C12Q 1/00* (2006.01)
*C12Q 1/37* (2006.01)

(52) U.S. Cl.
CPC ......... *G01N 27/3277* (2013.01); *C12Q 1/005* (2013.01); *C12Q 1/37* (2013.01); *G01N 33/5438* (2013.01)

(58) Field of Classification Search
CPC .. G01N 27/3277; G01N 33/5438; C12Q 1/37; C12Q 1/005
See application file for complete search history.

(56) References Cited

U.S. PATENT DOCUMENTS

| 5,912,114 A | 6/1999 | Hutchinson et al. |
| 6,814,844 B2 | 11/2004 | Bhullar et al. |
| 7,476,827 B1 | 1/2009 | Bhullar et al. |
| 7,780,827 B1 | 8/2010 | Bhullar et al. |

(Continued)

FOREIGN PATENT DOCUMENTS

| CA | 2763842 | 12/2010 |
| WO | 2010142037 | 12/2010 |

OTHER PUBLICATIONS

Chen Y, Ding J, Qin W. Potentiometric determination of trypsin using a polymeric membrane polycation-sensitive electrode based on current-controlled reagent delivery. Bioelectrochemistry. Dec, 2012, 88: 144-147.

(Continued)

*Primary Examiner* — John C Ball

(57) ABSTRACT

Electrochemical biosensing devices and methods detect the activity of proteases and active infection in biological samples. The devices and methods utilize distance constraints between a redox reporter and an electrode to create a change in current that is detected. The distance constraints are released when an analyte containing a specified protease or proteases reacts with a protein substrate sequence in the analyte. The particular protease or proteases to be detected can be selected by using biosensors with particular substrate sequences. The devices and methods are not only qualitative, they can be used to quantitatively evaluate protease content in samples.

18 Claims, 7 Drawing Sheets

(56) References Cited

U.S. PATENT DOCUMENTS

| | | | |
|---|---|---|---|
| 7,854,826 | B2 | 12/2010 | So et al. |
| 8,058,024 | B2 | 11/2011 | Schultz et al. |
| 8,592,167 | B2 | 11/2013 | Davis et al. |
| 8,734,631 | B2 | 5/2014 | Ahrens et al. |
| 8,802,390 | B2 | 8/2014 | Bertin et al. |
| 8,812,083 | B2 | 8/2014 | Papazoglou et al. |
| 8,846,328 | B2 | 9/2014 | Davis et al. |
| 8,951,400 | B2 | 2/2015 | Ahrens et al. |
| 8,969,027 | B2 | 3/2015 | Bossman et al. |
| 2005/0196820 | A1* | 9/2005 | Zweig .................... C12Q 1/004 435/14 |
| 2007/0154909 | A1* | 7/2007 | Xiao ..................... C12Q 1/6825 435/6.15 |
| 2012/0010099 | A1 | 1/2012 | Stephens et al. |
| 2012/0034638 | A1 | 2/2012 | Ahrens et al. |
| 2012/0156709 | A1 | 6/2012 | Bertin et al. |
| 2012/0285829 | A1 | 11/2012 | Mount et al. |
| 2013/0040848 | A1 | 2/2013 | Ko Ferrigno et al. |
| 2014/0027310 | A1 | 1/2014 | Gaustad et al. |

OTHER PUBLICATIONS

Abd-Rabboh HS, Nevins SA, Durust N, Meyerhoff ME. Electrochemical assay of protease activities based on polycation/polyanion complex as substrate and polyion sensitive membrane electrode detection. Biosensors & bioelectronics. Mar. 2003, 18(2-3): 229-236.

Munge BS, Fisher J, Millord LN, Krause CE, Dowd RS, Rusling JF. Sensitive electrochemical immunosensor for matrix metalloproteinase-3 based on single-wall carbon nanotubes. Analyst. Jun. 2010, 135(6): 1345-1350.

Liu G, Wang J, Wunschel DS, Lin Y. Electrochemical proteolytic beacon for detection of matrix metalloproteinase activities. Journal of the American Chemical Society. Sep. 27, 2006, 128(38): 12382-12383.

Liu Y, Kwa T, Revzin A. Simultaneous detection of cell-secreted TNF-alpha and IFN-gamma using micropatterned aptamer-modified electrodes. Biomaterials. Oct. 2012, 33(30): 7347-7355.

Liu Y, Yan J, Howland MC, Kwa T, Revzin A. Micropatterned aptasensors for continuous monitoring of cytokine release from human leukocytes. Analytical chemistry. Nov. 1, 2011, 83(21): 8286-8292.

Lai RY, Lagally ET, Lee SH, Soh HT, Plaxco KW, Heeger AJ. Rapid, sequence-specific detection of unpurified PCR amplicons via a reusable, electrochemical sensor. Proceedings of the National Academy of Sciences of the United States of America. Mar. 14, 2006, 103(11): 4017-4021.

Xia Z, Xing Y, So M-K, Koh AL, Sinclair R, Rao J. Multiplex detection of protease activity with quantum dot nanosensors prepared by Intein-mediated specific bioconjugation. Analytical Chemistry. Nov. 15, 2008, 80(22): 8649-8655.

Nagase H. Substrate specificity of MMPs. In: Matrix Metalloproteinase Inhibitors in Cancer Therapy. Eds: Clendeninn NJ, Appelt K. Humana Press, Totowa, New Jersey. 2001, pp. 39-66.

Chen EI, Kridel SJ, Howard EW, Li W, Godzik A, Smith JW. A unique substrate recognition profile for matrix metalloproteinase-2. The Journal of Biological Chemistry. Feb. 8, 2002, 277(6): 4485-4491.

Fields GB, Van Wart HE, Birkedal-Hansen H. Sequence specificity of human skin fibroblast collagenase: evidence for the role of collagen structure in determining the collagenase cleavage site. The Journal of Biological Chemistry. May 5, 1987, 262(13): 6221-6226.

Netzel-Arnett S, Fields G, Birkedal-Hansen H, Van Wart HE. Sequence specificities of human fibroblast and neutrophil collagenases. The Journal of Biological Chemistry. Apr. 15, 1991, 266(11): 6747-6755.

Netzel-Arnett S, Sang Q-X, Moore WGI, Navre M, Birkedal-Hansen H, Van Wart HE. Comparative sequence specificities of human 72- and 92-kDa gelatinases (type-IV collagenases) and PUMP (matrilysin). Biochemistry. 1993, 32(25): 6427-6432.

Sinha S, Watorek W, Karr S, Giles J, Bode W, Travis J. Primary structure of human neutrophil elastase. Proceedings of the National Academy of Sciences of the United States of America. Apr. 1987, 84: 2228-2232.

Dall'Acqua W, Halin C, Rodrigues ML, Carter P. Elastase substrate specificity tailored through substrate-assisted catalysis and phage display. Protein Engineering. 1999, 12(11): 981-987.

Jackson PL, Xu X, Wilson L, Weathington NM, Clancy JP, Blalock JE, Gaggar A. Human neutrophil elastase-mediated cleavage sites of MMP-9 and TIMP-1: Implications to cystic fibrosis proteolytic dysfunction. Molecular Medicine. May-Jun. 2010, 16(5-6): 159-166.

Kasperkiewicz P, Poreba M, Snipas SJ, Parker H, Winterbourn CC, Salvesen GS, Drag M. Design of ultrasensitive probes for human neutrophil elastase through hybrid combinatorial substrate library profiling. Proceedings of the National Academy of Sciences of the United States of America. Feb. 18, 2014, 111(7): 2518-2523.

Korkmaz B, Attucci S, Hazouard E, Ferrandière M, Jourdan ML, Brillard-Bourdet M, Juliano L, Gauthier F. Discriminating between the activities of human neutrophil elastase and proteinase 3 using serpin-derived fluorogenic substrates. The Journal of Biological Chemistry. Oct. 18, 2002, 277(42): 39074-39081.

Korkmaz B, Horwitz MS, Jenne DE, Gauthier F. Neutrophil elastase, proteinase 3, and cathepsin G as therapeutic targets in human diseases. Pharmacological Reviews. Dec. 2010, 62(4): 726-759.

Heinzle, A, Papen-Botterhuis NE, Schiffer D, Schneider KP, Binder B, Schintler M, Haaksman IK, Lenting HB, Gübitz GM, Sigl E. Novel protease-based diagnostic devices for detection of wound infection. Wound Repair and Regeneration. Jan. 30, 2013, 21: 482-489.

Williams BA, Lin L, Lindsay SM, Chaput JC. Evolution of a histone H4-K16 acetyl-specific DNA aptamer. Journal of the American Chemical Society. May 13, 2009, 131(18): 6330-6331.

Kambayashi Y, Nakao K, Mukoyama M, Saito Y, Ogawa Y, Shiono S, Inouye K, Yosida N, Imura H. Isolation and sequence determination of human brain natriuretic peptide in human atrium. FEBS Letters. Jan. 1990, 259(2): 341-345.

Astakhova IK, Hanson LH, Vester B, Wengel J. Peptide-LNA oligonucleotide conjugates. Organic & Biomolecular Chemistry. 2013, 11: 4240-4249.

Kolb HC, Finn MG, Sharpless KB. Click chemistry: diverse chemical function from a few good reactions. Angewandte Chemie International Edition in English. Jun. 1, 2001. 40(11): 2004-2021.

Hong V, Presolski SI, Ma C, Finn MG. Analysis and optimization of copper-catalyzed azide-alkyne cycloaddition for bioconjugation. Angewandte Chemie International Edition in English. 2009, 48(52): 9879-9883.

Presolski SI, Hong VP, Finn MG. Copper-catalyzed azide-alkyne click chemistry for bioconjugation. Current Protocols in Chemical Biology. Dec. 1, 2011, 3(4): 153-162.

Jewett JC, Bertozzi CR. Cu-free click cycloaddition reactions in chemical biology. Chemical Society Reviews. Apr. 2010, 39(4): 1272-1279.

Ess DH, Jones GO, Houk KN. Transition states of strain-promoted metal-free click chemistry: 1, 3-dipolar cycloadditions of phenyl azide and cyclooctynes. Organic Letters. Apr. 17, 2008, 10(8): 1633-1636.

Debets MF, van Berkel SS, Schoffelen S, Rutjes FP, van Hest JC, van Delft FL. Aza-dibenzocyclooctynes for fast and efficient enzyme PEGylation via copper-free (3+2) cycloaddition. Chemical Communications (Cambridge, England). Jan. 7, 2010, 46(1): 97-99.

Kuzmin A, Poloukhtine A, Wolfert MA, Popik VV. Surface functionalization using catalyst-free azide-alkyne cycloaddition. Bioconjugate Chemistry. Nov. 17, 2010, 21(11): 2076-2085.

Yao JZ, Uttamapinant C, Poloukhtine A, Baskin JM, Codelli JA, Sletten EM, Bertozzi CR, Popik VV, Ting AY. Fluorophore targeting to cellular proteins via enzyme-mediated azide ligatin and strain-promoted cycloaddition. Journal of the American Chemical Society. Feb. 29, 2012, 134(8): 3720-3728.

(56) References Cited

OTHER PUBLICATIONS

Liang Y, Mackey JL, Lopez SA, Liu F, Kouk KN. Control and design of mutual orthogonality in bioorthogonal cycloadditions. Journal of the American Chemical Society. Oct. 31, 2012, 134(43): 17904-17907.

Gogoi K, Mane MV, Kunte SS, Kumar VA. A versatile method for the preparation of conjugates of peptides with DNA/PNA/analog by employing chemo-selective click reaction in water. Nucleic Acids Research. 2007, 35(21) e139.

Golas PL, Matyjaszewski K. Marrying click chemistry with polymerization: expanding the scope of polymeric materials. Chemical Society Reviews. 2010, 39: 1338-1354.

Seckutē J, Devaraj NK. Expanding room for tetrazine ligations in the in vivo chemistry toolbox. Current Opinion in Chemical Biology. Oct. 2013, 17(5): 761-767.

Kane DP. Chronic wound healing and chronic wound management. In: Chronic Wound Care: A Clinical Resource Book for Healthcare Professionals, 4th edition. Krasner D.L., Rodeheaver G.T., Sibbald R.G., (eds.). Malvern, HMP Communications, 2007, pp. 11-24.

Mast BA, Schultz GS. Interactions of cytokines, growth factors, and proteases in acute and chronic wounds. Wound repair and regeneration: official publication of the Wound Healing Society [and] the European Tissue Repair Society. Oct. 1996, 4(4): 411-420.

Falanga V, Grinnell F, Gilchrest B, Maddox YT, Moshell A. Workshop on the pathogenesis of chronic wounds. The Journal of investigative dermatology. Jan. 1994, 102(1): 125-127.

World Union of Wound Healing Societies (WUWHS). Principles of best practice: Diagnostics and wounds a consensus document. London: MEP Ltd. 2008, Available from: http://www.woundsinternational.com/pdf/content_29.pdf.

International Consensus. The role of proteases in wound diagnostics an expert working group review. London: Wounds International. 2011, Available from: http://www.woundsinternational.com/pdf/content_9869.pdf.

Snyder RJ, Driver V, Fife CE, Lantis J, Peirce B, Serena T, Weir D. Using a diagnostic tool to identify elevated protease activity levels in chronic and stalled wounds: a consensus panel discussion. Ostomy/wound management. Dec. 2011, 57(12): 36-46.

Wysocki AB, Staiano-Coico L, Grinnell F. Wound fluid from chronic leg ulcers contains elevated levels of metalloproteinases MMP-2 and MMP-9. The Journal of investigative dermatology. Jul. 1993, 101(1): 64-68.

Utz ER, Elster EA, Tadaki DK, Gage F, Perdue PW, Forsberg JA, Stojadinovic A, Hawksworth JS, Brown TS. Metalloproteinase expression is associated with traumatic wound failure. The Journal of surgical research. Apr. 2010, 159(2): 633-639.

Ladwig GP, Robson MC, Liu R, Kuhn MA, Muir DF, Schultz GS. Ratios of activated matrix metalloproteinase-9 to tissue inhibitor of matrix metalloproteinase-1 in wound fluids are inversely correlated with healing of pressure ulcers. Wound repair and regeneration: official publication of the Wound Healing Society [and] the European Tissue Repair Society. Jan.-Feb. 2002, 10(1): 26-37.

Beidler SK, Douillet CD, Berndt DF, Keagy BA, Rich PB, Marston WA. Multiplexed analysis of matrix metalloproteinases in leg ulcer tissue of patients with chronic venous insufficiency before and after compression therapy. Wound repair and regeneration: official publication of the Wound Healing Society [and] the European Tissue Repair Society. Sep.-Oct. 2008, 16(5): 642-648.

Weiss SJ. Tissue destruction by neutrophils. The New England journal of medicine. Feb. 9, 1989, 320(6): 365-376.

Yager DR, Kulina RA, Gilman LA. Wound fluids: a window into the wound environment? The international journal of lower extremity wounds. Dec. 2007, 6(4): 262-272.

Costerton JW, Stewart PS, Greenberg EP. Bacterial biofilms: a common cause of persistent infections. Science. May 21, 1999, 284(5418): 1318-1322.

Webb JS, Givskov M, Kjelleberg S. Bacterial biofilms: prokaryotic adventures in multicellularity. Current opinion in microbiology. Dec. 2003, 6(6): 578-585.

Donlan RM. Role of biofilms in antimicrobial resistance. ASAIO journal (American Society for Artificial Internal Organs: 1992). Nov.-Dec. 2000, 46(6): S47-52.

Becker P, Hufnagle W, Peters G, Herrmann M. Detection of differential gene expression in biofilm-forming versus planktonic populations of *Staphylococcus aureus* using micro-representational-difference analysis. Applied and environmental microbiology. Jul. 2001, 67(7): 2958-2965.

Bollinger N, Hassett DJ, Iglewski BH, Costerton JW, McDermott TR. Gene expression in Pseudomonas aeruginosa: evidence of iron override effects on quorum sensing and biofilm-specific gene regulation. Journal of bacteriology. Mar. 2001, 183(6): 1990-1996.

Stewart PS, Costerton JW. Antibiotic resistance of bacteria in biofilms. Lancet. Jul. 14, 2001, 358(9276): 135-138.

Vallet I, Olson JW, Lory S, Lazdunski A, Filloux A. The chaperone/usher pathways of Pseudomonas aeruginosa: identification of fimbrial gene clusters (cup) and their involvement in biofilm formation. Proceedings of the National Academy of Sciences of the United States of America. Jun. 5, 2001, 98(12): 6911-6916.

Whiteley M, Bangera MG, Bumgarner RE, Parsek MR, Teitzel GM, Lory S, Greenberg EP. Gene expression in Pseudomonas aeruginosa biofilms. Nature. Oct. 25, 2001, 413(6858): 860-864.

Donlan RM. Biofilms: microbial life on surfaces. Emerging infectious diseases. Sep. 2002, 8(9): 881-890.

Donlan RM, Costerton JW. Biofilms: survival mechanisms of clinically relevant microorganisms. Clinical microbiology reviews. Apr. 2002, 15(2): 167-193.

Parsek MR, Singh PK. Bacterial biofilms: an emerging link to disease pathogenesis. Annual review of microbiology. 2003, 57: 677-701.

Smith RS, Iglewski BH. P. aeruginosa quorum-sensing systems and virulence. Current opinion in microbiology. Feb. 2003, 6(1): 56-60.

Head NE, Yu H. Cross-sectional analysis of clinical and environmental isolates of Pseudomonas aeruginosa: biofilm formation, virulence, and genome diversity. Infection and immunity. Jan. 2004, 72(1): 133-144.

Ren D, Bedzyk LA, Thomas SM, Ye RW, Wood TK. Gene expression in *Escherichia coli* biofilms. Applied microbiology and biotechnology. May 2004, 64(4): 515-524.

Leid JG, Costerton JW, Shirtliff ME, Gilmore MS, Engelbert M. Immunology of Staphylococcal biofilm infections in the eye: new tools to study biofilm endophthalmitis. DNA and cell biology. May-Jun. 2002, 21(5-6): 405-413.

Leid JG, Kerr M, Selgado C, Johnson C, Moreno G, Smith A, Shirtliff ME, O'Toole GA, Cope EK. Flagellum-mediated biofilm defense mechanisms of Pseudomonas aeruginosa against host-derived lactoferrin. Infection and immunity. Oct. 2009, 77(10): 4559-4566.

Leid JG, Shirtliff ME, Costerton JW, Stoodley P. Human leukocytes adhere to, penetrate, and respond to *Staphylococcus aureus* biofilms. Infection and immunity. Nov. 2002, 70(11): 6339-6345.

Leid JG, Willson CJ, Shirtliff ME, Hassett DJ, Parsek MR, Jeffers AK. The exopolysaccharide alginate protects Pseudomonas aeruginosa biofilm bacteria from IFN-gamma-mediated macrophage killing. Journal of immunology. Dec. 1, 2005, 175(11): 7512-7518.

Wolcott RD, Rhoads DD, Bennett ME, Wolcott BM, Gogokhia L, Costerton JW, Dowd SE. Chronic wounds and the medical biofilm paradigm. Journal of wound care. Feb. 2010, 19(2): 45-46, 48-50, 52-43.

James GA, Swogger E, Wolcott R, Pulcini E, Secor P, Sestrich J, Costerton JW, Stewart PS. Biofilms in chronic wounds. Wound repair and regeneration: official publication of the Wound Healing Society [and] the European Tissue Repair Society. Jan.-Feb. 2008, 16(1): 37-44.

Mok W, Li Y. Recent progress in nucleic acid aptamer-based biosensors and bioassays. Sensors. Nov. 7, 2008, 8: 7050-7084.

McKeague M, DeRosa MC. Challenges and opportunities for small molecule aptamer development. Journal of Nucleic Acids. vol. 2012: Article ID 748913, 20 pages. doi: 10.1155/2012/748913.

Rowe AA, Chuh KN, Lubin AA, Miller EA, Cook B, Hollis D, Plaxco KW. Electrochemical biosensors employing an internal

(56) References Cited

OTHER PUBLICATIONS electrode attachment site achieve reversible, high gain detection of specific nucleic acid sequences. Analytical Chemistry. Dec. 15, 2011, 83(24): 9462-9466.

Shin D-S, Liu Y, Gao Y, Kwa T, Heller A, Matharu Z. Revzin A. Micropatterned surfaces functionalized with electroactive peptides for detecting protease release from cells. Analytical Chemistry. Jan. 2, 2013, 85(1): 220-227.

Danesh NM, Ramezani M, Emrani AS, Abnous K, Taghdisi SM. A novel electrochemical aptasensor based on arch-shape structure of aptamer-complimentary strand conjugate and exonuclease I for sensitive detection of streptomycin. Biosensors and Bioelectronics. Jan. 15, 2016, 75: 123-128.

Taleat Z, Cristea C, Marrazza G, Mazloum-Ardakani M, Săndulescu R. Electrochemical immunoassay based on aptamer-protein interaction and functionalized polymer for cancer biomarker detection. Journal of Electroanalytical Chemistry. Mar. 15, 2014, 717-718: 119-124.

Li B, Li Z, Situ B, Dai Z, Liu Q, Wang Q, Gu D, Zheng L. Sensitive HIV-1 detection in a homogeneous solution based on an electrochemical molecular beacon coupled with a nafion-graphene composite film modified screen-printed carbon electrode. Biosensors and Bioelectronics. Feb. 15, 2014, 52: 330-336.

Feldman B, McGarraugh G, Heller A, Bohannon N, Skyler J, DeLeeuw E, Clarke D. FreeStyle: a small-volume electrochemical glucose sensor for home blood glucose testing. Diabetes technology & therapeutics. Summer, 2000, 2(2): 221-229.

Alva S. FreeStyle Lite—a blood glucose meter that requires no coding. Journal of diabetes science and technology. Jul. 2008, 2(4): 546-551.

Guerreiro G, Zaitouna AJ, Lai RY. Characterization of an electrochemical mercury sensor using alternating current, cyclic, square wave and differential pulse voltammetry. Analytica Chimica Acta 2014, 810: 79-85.

Li G, Miao P. Theoretical background of electrochemical analysis. In: Electrochemical analysis of proteins and cells. Springer-Verlag, Berlin Heidelberg. 2013, pp. 5-18.

Yang w, Lai RY. Comparison of the stem-loop and linear probe-based electrochemical DNA sensors by alternating current voltammetry and cyclic voltammetry. Langmuir. 2011, 27(23): 14669-14677.

Bonham AJ, Hsieh K, Ferguson BS, Vallée-Bélisle A, Ricci F, Soh HT, Plaxco KW. Quantification of transcription factor binding in cell extracts using an electrochemical, structure-switching biosensor. Journal of the American Chemical Society. Feb. 22, 2012, 134(7): 3346-3348.

Vallée-Bélisle A, Ricci F, Uzawa T, Xia F, Plaxco KW. Bioelectrochemical switches for the quantitative detection of antibodies directly in whole blood. Journal of the American Chemical Society. Sep. 19, 2012, 134(37): 15197-15200. doi: 10.1021/ja305720w.

Baker BR, Lai RY, Wood MS, Doctor EH, Heeger AJ, Plaxco KW. An electronic, aptamer-based small-molecule sensor for the rapid, label-free detection of cocaine in adulterated samples and biological fluids. Journal of the American Chemical Society. Mar. 15, 2006, 128(10): 3138-3139.

Xiao Y, Lubin AA, Heeger AJ, Plaxco KW. Label-free electronic detection of thrombin in blood serum by using an aptamer-based sensor. Angewandte Chemie. Aug. 26, 2005, 44(34): 5456-5459.

Radi AE, Acero Sanchez JL, Baldrich E, O'Sullivan CK. Reagentless, reusable, ultrasensitive electrochemical molecular beacon aptasensor. Journal of the American Chemical Society. Jan. 11, 2006, 128(1): 117-124.

Xiao Y, Piorek BD, Plaxco KW, Heeger AJ. A reagentless signal-on architecture for electronic, aptamer-based sensors via target-induced strand displacement. Journal of the American Chemical Society. Dec. 28, 2005, 127(51): 17990-17991.

* cited by examiner

METHOD FOR DETECTING PROTEASES AND ACTIVE INFECTION IN BIOLOGICAL FLUIDS AND TISSUES

CROSS-REFERENCE TO RELATED APPLICATIONS

This application claims the benefit of U.S. Provisional Application No. 62/065,440, filed Oct. 17, 2014.

STATEMENT REGARDING FEDERALLY SPONSORED RESEARCH OR DEVELOPMENT

Not Applicable

THE NAMES OF PARTIES TO A JOINT RESEARCH AGREEMENT

Not Applicable

REFERENCE TO AN ELECTRONIC SEQUENCE LISTING

The contents of the electronic sequence listing (14887291_Wardell_Sequence_Listing_Prime_V5.txt; Size: 32,544 bytes; and Date of Creation: Apr. 27, 2018) is herein incorporated by reference in its entirety.

BACKGROUND OF THE INVENTION

Field of the Invention

The invention broadly relates to electrochemical biosensing, more specifically to an electrochemical biosensing device to detect the activity of proteases and active infection in biological fluids and tissues, and even more particularly to a method of electrochemical biosensing to detect the activity of proteases and active infection in biological fluids and tissues.

Description of the Related Art

Differentiated from acute wounds that heal in a matter of days or weeks, chronic wounds persist for months or years and, may, last a lifetime. Such chronic wounds are commonly referred to as non-healing wounds. Examples include diabetic foot ulcers, venous leg ulcers, and pressure ulcers, and other types of chronic wounds including arterial ulcers, non-healing surgical wounds, burns, fistulae, dermatitis or vasculitis wounds, skin cancers, and radiation wounds. Unlike acute wounds that progress through the four normal phases of healing (hemostasis, inflammation, proliferation, and remodeling), chronic wounds stall in their healing, often in the inflammatory phase. Wounds fail to heal because molecular and cellular abnormalities in the wound prevent healing progress.

Over the past decade, expert panels have met at international wound meetings to report the importance of effective assessment and diagnosis in the treatment of wounds. The first such international group of experts met in June, 2007, with the intent that their report would serve as a platform to stimulate the development of dedicated test kits that would beneficially influence the future management of problem wounds. This panel concluded that specific biochemical tests were urgently needed that would identify the causes of delayed healing in wounds that are slow-to-heal and that the most appropriate markers to serve as biochemical indicators of stalled wound healing would include elevated proteases, infection, and perhaps decreased nitric oxide.

A second panel of experts of international recognition convened in February, 2011, and confirmed the need for biochemical wound diagnostics and identified elevated wound proteases as an important biochemical target. This panel also determined that an easy to use, point-of-care protease diagnostic would be of immense value in clinical practice. A third expert panel also convened in May, 2011, and concluded that wound protease levels would be a useful marker to help direct clinicians to specific treatments. The proteases most often elevated in non-healing wounds that are often stalled in an inflammatory state include matrix metalloproteinases, especially collagenases and gelatinases, and serine proteases, especially neutrophil serine proteases. The literature indicates that multiple matrix metalloproteinases (MMPs) are associated with stalled wound healing. These proteases are normal contributors to the early inflammatory phase of wound healing, to degrade damaged tissue and help prepare a clean wound bed for healing. But this activity normally occurs within three to five days after which the activities of these proteases reduce to very low levels in the wound environment. However, in non-healing wounds elevated levels of proteases persist and they continue to degrade extracellular matrix, growth factors and receptors involved in wound healing. This causes the wound not to fully heal.

Multiple matrix metalloproteinases contribute to stalled wound healing including the gelatinases, MMP-2, and MMP-9; the collagenases MMP-1, MMP-8, and MMP-13; stromelysin, MMP-3; and matrilysin, MMP-7. Whereas some researchers tried to identify one of these to provide the best target for diagnostic test development, other researchers have proposed that the measurement of just one individual protease would be unlikely to be representative of the proteolytic environment of the wound. Although there have now been 25 MMPs described and classified, partly on historical assessment of the substrate specificity of the MMP (and partly on the cellular localization of each), it has become increasingly clear that there is a lot of overlap in their substrate specificities. This is not surprising since structural analysis of the catalytic domains of many MMPs revealed that their polypeptide folds are essentially superimposable. Furthermore, it has been shown that substrate specificities that might exist in their natural substrates further break down when short peptide substrates are used, due to the loss of secondary and tertiary structure that only exists in the full-length natural protein substrates. Peptide substrates have been identified that can be cleaved by multiple wound MMPs, and these promiscuous substrates would make appropriate reagents for a more representative determination of the total proteolytic activity in the wound environment.

In addition to the presence of elevated MMP proteases in a wound, a large body of work has also identified that infection of wounds is also a major factor that prevents them from healing. Common wound pathogens include, but are not limited to, *Staphylococcus aureus* (including MRSA) and *Pseudomonas aeruginosa*. These bacteria exist in two major forms: either free-living single cells known as planktonic form, or as biofilm communities. Whereas planktonic bacteria are relatively easy to control (unless they consist of superbugs such as MRSA [Methicillin-resistant *Staphylococcus aureus*], C. Diff [*Clostridium difficile*], VRE [Vancomycin-resistant *Enterococci*], CRE [Carbapenem-resistant Enterobacteriaceae] and CRKP [Carbapenem-resistant *Klebsiella* pneumonia]), bacterial biofilms are much more difficult to remove.

A biofilm is an assemblage of microbial cells that is irreversibly associated with a surface and is most often enclosed in a matrix of primary polysaccharide material often referred to as 'slough' in chronic wounds. Biofilm-associated organisms differ from their planktonic counterparts in the genes that are transcribed, resulting in an altered resistance to antibiotics and the human immune system. A biofilm colony is more similar to a multicellular organism with cell-cell interaction and communication and division of labor, and this makes such colonies very difficult to kill and control. In a biofilm colony there are some bacteria that are growing and reproducing and making the matrix they live in, while other cells exist in a protective, sprawling state that are relatively quiescent, but in the event of a catastrophic challenge, those cells can survive and re-seed the biofilm. For example, biofilm can often reestablish within twenty four (24) hours following removal by surgical debridement.

Biofilm in wounds has become a significant problem. It has been estimated that up to sixty percent (≤60%) of non-healing wounds contain biofilm but it is difficult to diagnose. Some researchers suggest measuring wounds for the presence of common wound bacteria, but others point out that just as they are present on normal skin surfaces all over the human body, commensal bacteria also exist on wound surfaces that are not causing active infection. A diagnostic that cannot distinguish between an active infection and a passive microbial colonization is of little use as an indicator of the state of the wound with respect to whether the presence of microbes is preventing the wound from healing.

As used herein, an 'active' infection is an infection caused by microorganisms, whether planktonic or associated in biofilm communities, that are maintaining a chronic state of wound inflammation or contributing to wound deterioration and preventing wound healing. Other suggestions for detecting the presence of biofilm include measuring components of the biofilm matrix, including polysaccharide, proteinaceous, or nucleic acid components. Such measurements, however, miss active infection caused by planktonic bacteria, and there are other problems with using such targets.

There is a need for an invention that recognizes that a better indicator of active infection than bacteria or their constituents is a measurement of the stressful response of the host to the presence of active infection. In response to a microbial infection, the host mounts a rapid multi-faceted immune response. For the purposes of the present invention, this includes the sending of neutrophil granulocytes, which are an abundant type of white blood cells adept at killing and phagocytosing microorganisms and other foreign material. Neutrophils (also known as leukocytes) are one of the first responders of inflammatory cells to migrate towards sites of inflammation. They migrate through the blood vessels, then through interstitial tissue, following chemical signals from pro-inflammatory cytokines such as Interleukin-1 (IL-1), IL-8, and tumor necrosis factor-alpha (TNF-α), in a process called chemotaxis. While some have suggested the detection of the pro-inflammatory cytokines as suitable targets for the diagnosis of infection, there is still a need to measure the activity of host proteases as a more informative analyte. This is because the host proteases released from neutrophils are closest to describing the effects of infection because they are the specific entities performing the tissue damage. In addition, the concentrations of cytokines are much lower and therefore more difficult to detect and interpret.

When neutrophils encounter a bacterial cell or foreign body, they become activated where they first initiate an oxidative attack against the bacterial cell wall and then release granules from their cytoplasm containing high concentrations of proteases into the bacteria through the hole in its outer cell membrane caused by the oxidative burst. These neutrophil proteases lead to the death of the pathogen by breaking down critical proteins inside the bacteria. Neutrophils also recognize biofilm as foreign and mount their attack against it, but the bacteria can 'hide' within the biofilm matrix, inaccessible to and protected from both the oxidative burst and the neutrophil proteases. The chronic presence of the biofilm colony causes the host's immune system to continually send neutrophils to try to remove it, resulting in high local concentrations of proteases in the wound, released from the activated neutrophils, and these cause significant damage to host tissue.

This process occurs in non-healing (chronic) wounds causing degradation of newly developing extracellular matrix, but it also occurs in other host tissues resulting in multiple disease states including, but not limited to, chronic obstructive pulmonary disease, COPD, including chronic bronchitis and emphysema, and periodontitis (destruction of gum tissue). The most notable proteases contributing to this tissue damage by the host's own attack response are the neutrophil serine proteases (NSPs) secreted from neutrophil azurophilic granules including neutrophil elastase, proteinase-3, and cathepsin G.

Accordingly, there is a long-felt need for a device and method for detecting the activity of proteases and active infection in biological fluids and tissues.

BRIEF SUMMARY OF THE INVENTION

An object of the present invention is to provide an electrochemical biosensing device for detecting both elevated proteases and active infections in biological fluids and tissues by controlling distance constraints between a redox reporter and a biosensor electrode.

Another object of the present invention is to provide a method of electrochemical biosensing detection of both elevated proteases and active infections in biological fluids and tissues by controlling distance constraints between a redox reporter and a biosensor electrode.

A general object of the present invention is to detect and provide a quantitative measurement of both elevated proteases and active infections in chronic, non-healing wounds.

It is yet another object of the present invention to provide an electrochemical biosensor to detect both elevated proteases and active infections in chronic, non-healing wounds.

The use of the present invention is most importantly demonstrated in patients with non-healing wounds containing protease activities higher than normal. Such patients typically have weekly appointments with their wound care providers, and the point-of-care diagnostic test of the present invention will be administered at each patient visit to indicate whether the protease activity level has increased, stayed the same, or decreased since the last visit. By quantitatively measuring the protease activity level, the present invention indicates the efficacy of the chosen treatment strategy over time. If the elevated protease activity has decreased since the previous visit, the wound care provider and the patient are encouraged that the adopted treatment strategy is successfully contributing to the conversion of the non-healing wound onto a healing trajectory. If the protease activity level has not decreased since the last patient visit, or if it has increased, it would indicate to the wound care provider that the treatment strategy needs to be adjusted. Through this quantitative analysis, the present invention provides early, accurate point-of-care information to help guide the week-by-week management of the wound. By providing a quantitative measurement of wound protease activity at each patient visit, the present invention offers a unique advantage for the navigational direction of wound management.

There are currently several therapeutic dressings designed to lower wound proteases. These include but are not limited to collagen/oxidized regenerated cellulose (e.g. Promogran by Systagenix), EDTA (e.g. Biostep by Smith & Nephew), and PHI (e.g. Tegaderm Matrix by 3M) dressings. The present invention indicates whether one of these or other protease-lowering therapies is beneficial to use, and furthermore, after some time of use, whether the chosen therapy is effectively lowering the wound protease activity levels. The present invention indicates in a more-timely manner than the presently used subjective observation by the wound care provider, whether the treatment strategy is working or should be changed to another protease-lowering therapy. Also, the present invention indicates when additional treatment strategies, described below, not indicated when wound protease levels are elevated, can be incorporated in the management strategy.

For example, present-day advanced wound therapies include the use of growth factors (e.g. Becaplermin [Regranex] platelet-derived growth factor by Smith & Nephew) and skin substitutes (e.g. Apligraf and Dermagraft, both by Organogenesis) that are both expensive. Both growth factor and skin substrate therapeutic modalities are readily susceptible to proteolysis, such that if they are applied to wounds still containing high protease activities, they will be destroyed before providing any therapeutic effect. The present invention provides an important tool to wound care providers contemplating wound therapy using either growth factors or skin substitutes (living skin equivalent or LSE). The present invention provides to wound care providers, for the first time, a reliable quantitative measurement of wound protease activity to indicate whether the wound is receptive to growth factor or LSE treatment. This quantitative information provides an important corollary to designing and justifying subsequent wound treatments as required by the majority of insurance corporations.

A further object of the invention is to detect active infection. Active infection is detected by the host stress response as determined by the release of large amounts of serine proteases from neutrophils (NSPs) recruited to inflamed and diseased tissue sites via chemotaxis. Specifically sites of infection recruit blood neutrophils, which release neutrophil serine proteases (NSPs) to attack the pathogenic organisms contributing to the infection. In an example embodiment, the measurement of these NSPs using the methods of the present invention indicate the host's stress level to the presence of active infection, and provide quantitative information to guide the infection management strategy. Infection therapeutic strategies including antibiotic administration and antibiofilm management are available, and are indicated by the elevated levels of NSPs by the present invention.

Electrochemical detection using biosensors in various configurations has been proposed for the detection of specific target molecules involved in multiple biological processes, including the diagnosis of disease. Most widely known is the electrochemical detection and monitoring of blood glucose for the management of diabetes. Electrochemical detection has also been proposed for the detection of other analytes including antibodies in whole blood; cocaine and other drug detection in biological fluids; proteases such as thrombin, trypsin and plasmin, endopeptidase neurotoxins, prostate specific antigen, MMP-3 as a cancer biomarker and MMP-7; cytokines, including interferon (IFN)-$\gamma$ and tumor necrosis factor (TNF)-$\alpha$; and detection of unpurified PCR amplification products of microbial pathogen DNA.

Detecting methods include, but are not limited to, potentiostatic measurement via either voltammetric methods, such as alternating current voltametry, linear sweep voltametry, cyclic voltametry, square wave voltametry, differential pulse voltametry, normal pulse voltametry, differential normal pulse voltametry, or amperometric methods, such as amperometric detection, fast amperometry, pulsed amperometric detection, and zero resistance amperometry. Alternatively, a galvanostatic measurement system could be used, such as linear sweep potentiometry, cyclic potentiometry, potentiometric detection (galvanostatic), fast potentiometry, zero current potentiometry, potentiometric stripping analysis, either galvanostatic or faradaic.

The invention can be applied for the detection and quantitation of elevated protease activity and active infection within wounds, as indications of stalled healing in chronic wounds such as diabetic foot ulcers, venous leg ulcers, pressure ulcers, arterial ulcers, wounds of mixed etiology, burns, non-healing surgical wounds and others. But the present invention is also applicable to other disease states involving elevated proteases resulting from a host stress response, such as gingivitis and periodontitis, chronic obstructive pulmonary disease (e.g. emphysema or chronic bronchitis), and other disorders.

These and other objects and advantages of the present invention will be readily appreciable from the following description of preferred embodiments of the invention and from the accompanying drawings and claims.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. It should be appreciated that the term "sample" is synonymous with terms such as "fluid", "detection device" is synonymous with terms such as "meter", and such respective terms may be used interchangeably as appearing in the specification and claims. Although any methods, devices or materials similar or equivalent to those described herein can be used in the practice or testing of the invention, the preferred methods, devices, and materials are now described.

Figure 1:
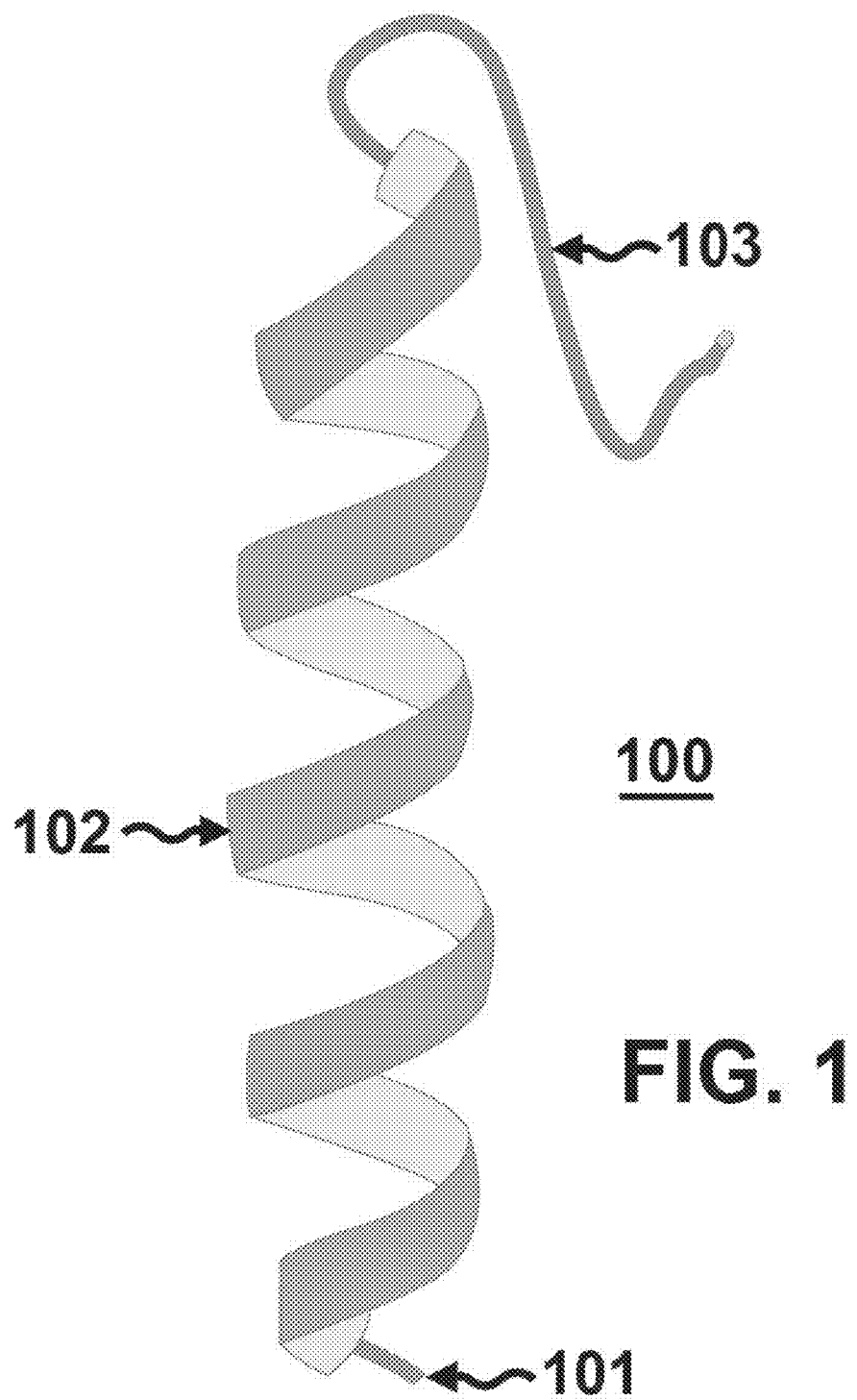
FIG. 1 is a computer generated model of lifting peptide SEQ ID NO: 48, an $\alpha$-helix 102 with the attachment cysteine on the bottom of the figure at the amino-terminus 101 and promiscuous MMP substrate SEQ ID NO: 3 constituting a open loop 103 at the carboxyl-terminal end of the construct at the top of the figure. This model was generated using PEP-FOLD where SEQ ID NO: 48 was predicted to be an $\alpha$-helix in most models, in agreement with its native structure in apolipoprotein E.
Figure 2:
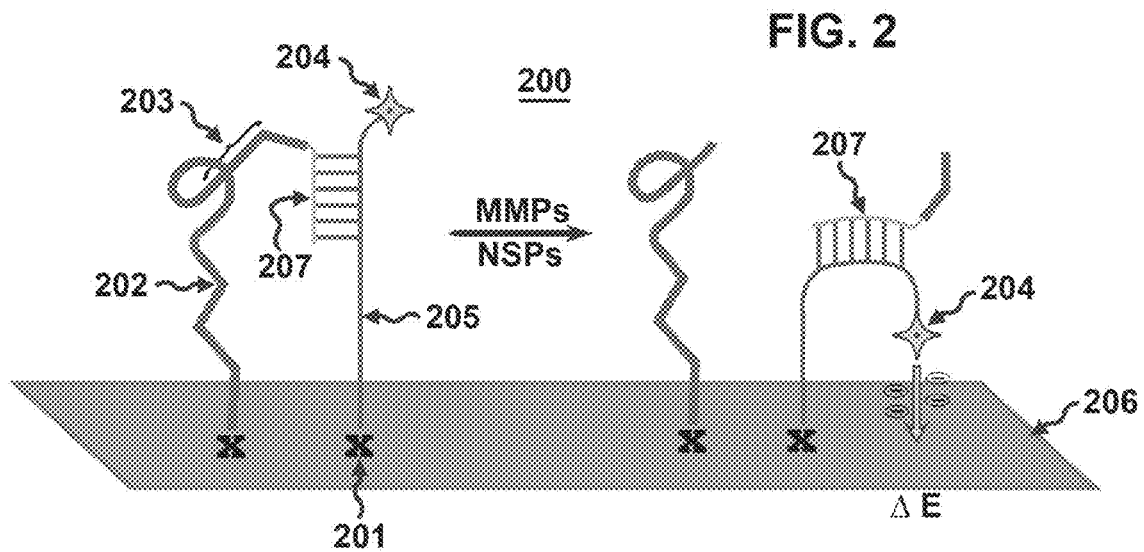
FIG. 2 is a first embodiment of an electrochemical biosensor according to the invention utilizing a peptide-oligonucleotide conjugate bound to a signaling oligonucleotide, showing before and after protease cleavage.

Adverting now to the figures, FIG. 1 is a computer-generated structure of a lifting peptide based on SEQ ID NO: 48, 102, which holds MMP and/or NSP peptide substrate sequence 103 above a biosensor electrode in an accessible position for proteolysis, and ultimately lifts a redox reporter above the biosensor electrode preventing current from flowing prior to proteolysis by sample proteases. This 'signal-on' configuration is represented in FIG. 2.

Figure 3:
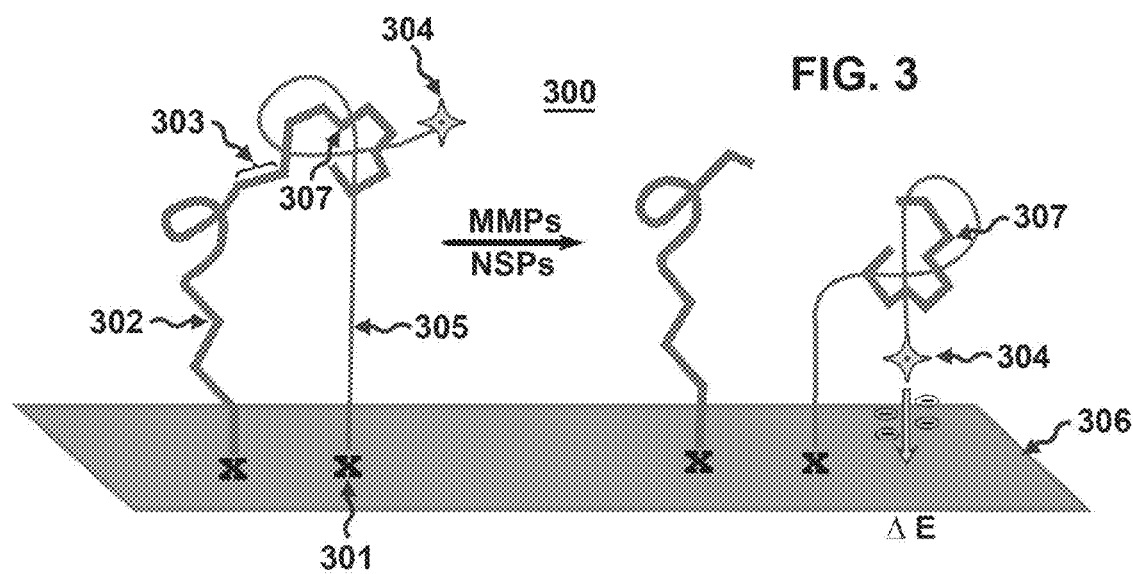
FIG. 3 is a second embodiment of an electrochemical biosensor according to the invention utilizing an aptamer recognition peptide bound to a signaling aptamer, showing before and after protease cleavage.
Figure 4:
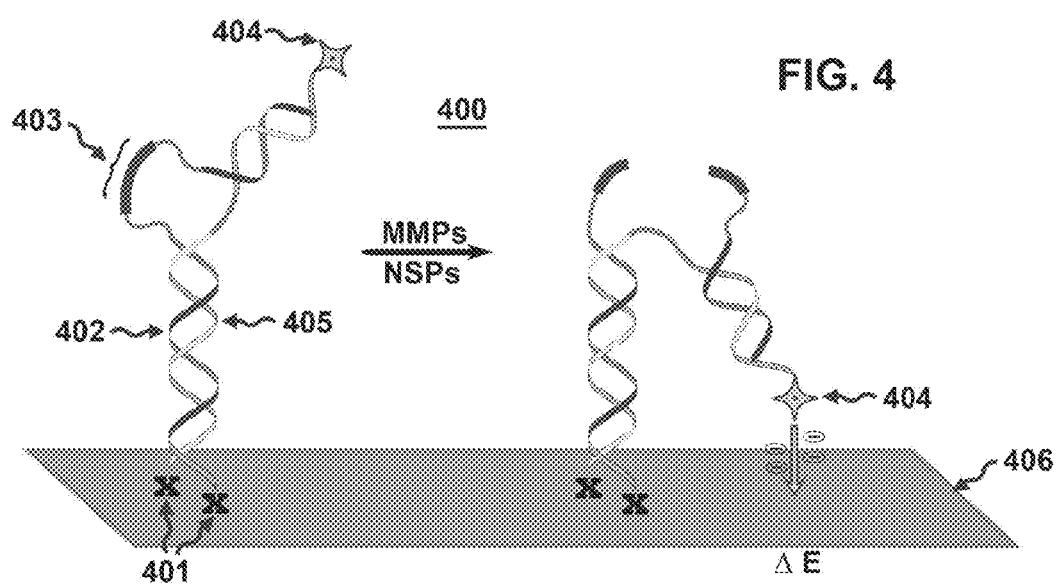
FIG. 4 is a third embodiment of an electrochemical biosensor according to the invention utilizing an oligonucleotide-peptide-oligonucleotide conjugate bound to a signaling oligonucleotide, showing before and after protease cleavage.

Two other lifting mechanisms are shown in FIGS. 3 and 4, where the protease cleavage sites 303 and 403, respectively, and redox reporters 304 and 404, respectively, are initially held above the working electrode 601 or 709 in a 'signal-on' configuration by either an aptamer recognition lifting peptide 302 bound to a signaling aptamer 305, or by a double-stranded DNA constituted by an oligonucleotide-peptide-oligonucleotide conjugate 402 bound to a signaling oligonucleotide 405, respectively.

Figure 5:
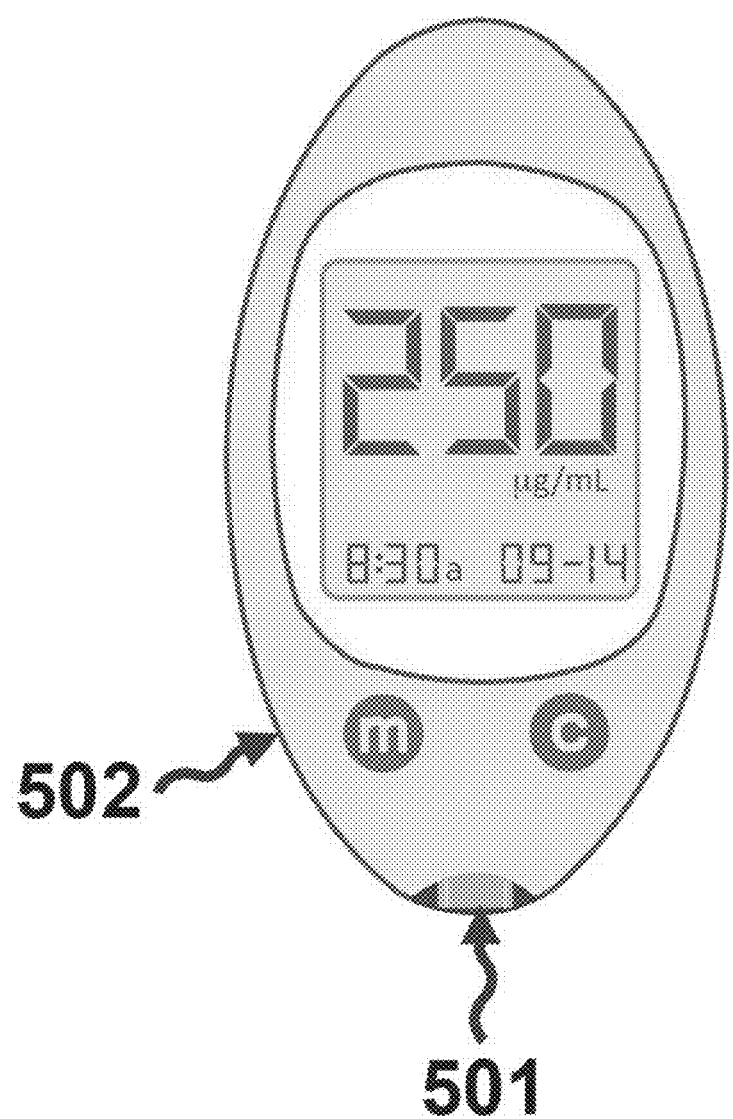
FIG. 5 is a front view of the electrical meter of the diagnostic device of the present invention.
Figure 6:
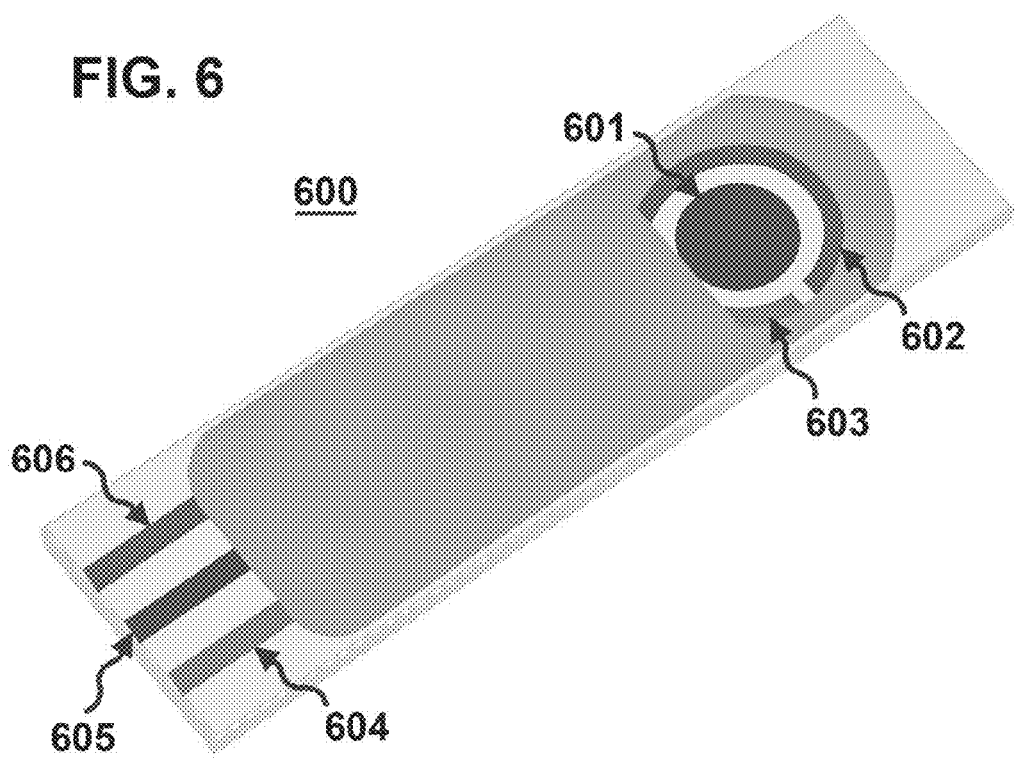
FIG. 6 is a front view of a diagnostic test strip of the diagnostic device that could be used with the electrical meter depicted in FIG. 5; the test strip uses manual addition of a specific volume of biological sample.
Figure 7:
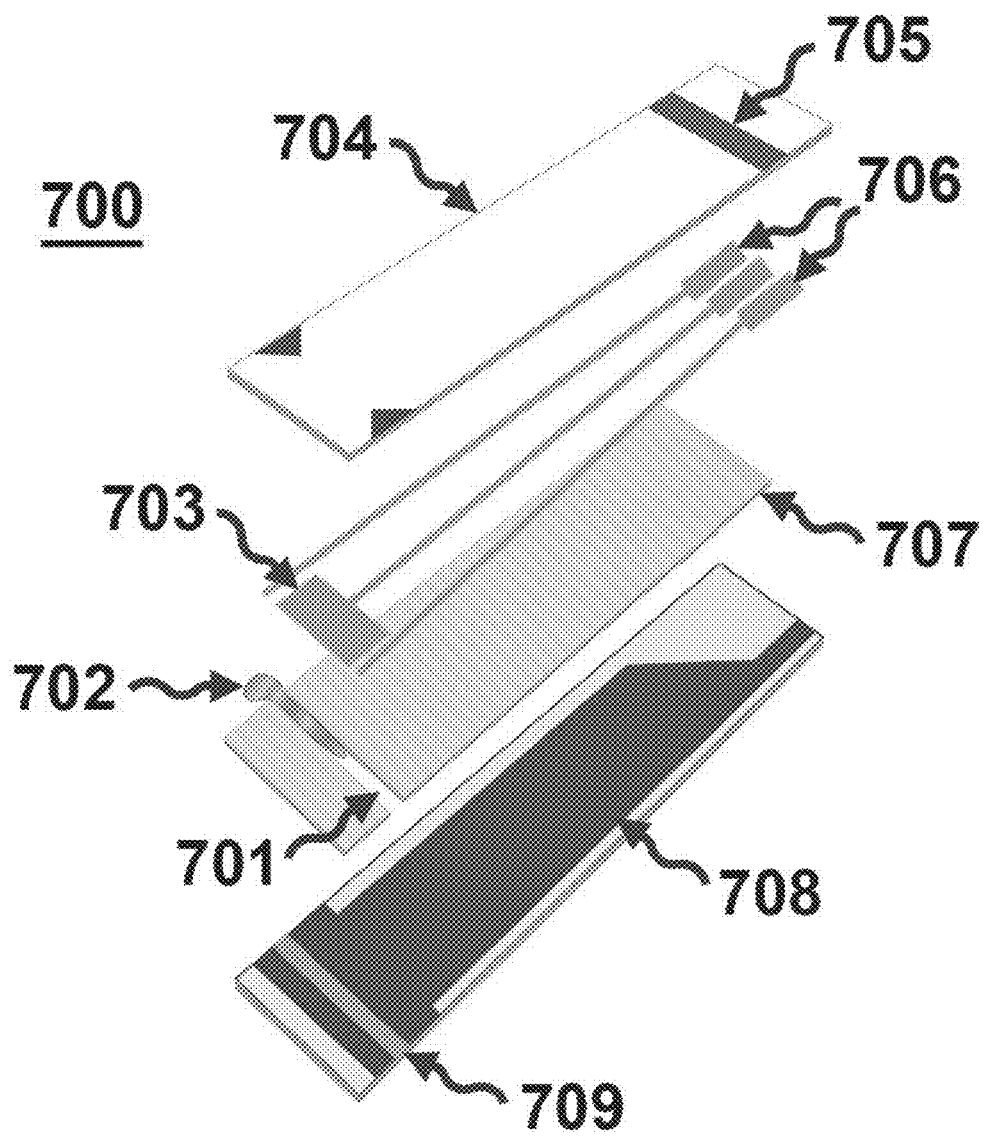
FIG. 7 is an exploded view of a diagnostic test strip of the diagnostic device used with the electrical meter depicted in FIG. 5; the test strip uses automatic addition of a specific volume of biological sample.

As shown in FIGS. 1-7, the present invention provides for a quantitative measurement of protease activity using a small and reproducible quantity of a biological sample 702. FIGS. 5-7 illustrate the electrical meter 502 and diagnostic test strips 600 and 700 that use an electrochemical biosensor, either 200, 300, or 400, which is free of optical detection limitations, and is based on a distance constraint mechanism to hold a redox reporter 204, 304, or 404 above an electrode 206, 306, or 406 prior to proteolysis by sample proteases. The molecular architecture provides for three example embodiments: 1) a lifting peptide-oligonucleotide conjugate (PepOliCon) 202 bound to a signaling oligonucleotide 205, shown in FIG. 2; 2) a lifting peptide coupled to a specific aptamer-recognition peptide sequence (aptamer epitope) 302 bound to a signaling aptamer 305, shown in FIG. 3; and 3) a lifting double-stranded DNA structure constituted by a portion of an oligonucleotide-peptide-oligonucleotide (OligoPepOligo) conjugate 402 and a complementary portion of a signaling oligonucleotide 405, shown in FIG. 4. All three embodiments provide the mechanism to lift the respective redox reporter 204, 304, or 404 on the terminus of the signaling oligonucleotide/aptamer 205, 305, or 405 high enough above the electrode 206, 306, or 406 of the electrochemical biosensor 200, 300, or 400 so as to initially inhibit current flow through the working electrode connection 605 or 708. Although FIG. 5 illustrates units of measurement as micrograms per milliliter (µg/mL), other measurement units are acceptable. The electrical meter 502 measures the protease activity as a concentration when diagnostic test strip 600 or 700 is inserted into slot 501 and has a biological sample 702 applied to the diagnostic test strip 700.

FIG. 6 shows an example configuration of a test strip 600 that is commercially available from multiple suppliers and which could be used in the present invention. This test strip configuration (constituted by a working electrode 601, a counter-electrode 602, and a reference electrode 603, with respective connectors 605, 606, and 604 that make contact inside electrical meter 502 when correctly inserted into slot 501) would require manual sample acquisition and application of an accurate amount of sample to working electrode 601. Such accurate sample acquisition and application could be made by a micropipette or capillary tube, or such other method as would be known to one skilled in the art.

FIG. 7 shows the structure of test strip 700. Test strip 700 is similar to that described by Alva 2008, includes multiple layers and could be custom-made for the present invention. The following description of test strip 700 in FIG. 7 starts at the top layer 704 and progresses downward to the bottom layer that contains electrochemical biosensor 709 and working electrode connector 708. The top layer 704 of test strip 700 includes the initializing bar 705. The next layer includes sample volume indicator electrodes 706 and reference electrode 703. Underneath this is a spacer layer 707 with a calibrated sample acquisition channel 701 of controlled dimensions. Sample channel slot 701 within spacer 707 draws a reproducible volume of biological sample 702 via capillary action over the biosensor 709 to facilitate the reaction between proteases in the sample 702 and the reagents on the biosensor 709. Underneath spacer 707 is the bottom layer, containing the electrochemical biosensor 709 working electrode where the chemistry takes place. Proteolytic cleavage of the biosensor reagent allows the redox tag to collide with the electrode surface (as shown in FIGS. 2-4), producing a readily detectable Faradaic current (ΔE) that travels down a connector of the working electrode 708 to the electrical meter 500. The electrochemical biosensor utilizes an electrode strip 206, 306, or 406, which can be constructed of various materials, including but not limited to, gold, platinum, carbon, nation-coated carbon, and polymers of such materials. The chemical reaction takes place on the electrode strip 206, 306, or 406 when there are proteases in the biological sample. The resulting faradaic current (ΔE) is directly proportional to the concentration of active proteases in the sample and therefore provides an accurate quantification of sample protease activity.

As depicted in FIG. 7, the orientation of the multiple layers of test strip 700 are strategically aligned for the detection process. For instance, initializing bar 705 is located at one end of test strip 700 for insertion into detection input slot 501 of the electrical meter 502 depicted in FIG. 5. When test strip 700 is placed into detection input slot 501 of the electrical meter 502, initializing bar 705 turns on the electrical meter 502. The opposing end of test strip 700 includes sample channel slot 701, into which biological sample 702 is drawn by capillary action to be deposited above electrochemical biosensor 709.

A volume of biological sample 702 is controlled by dimensions of the sample channel slot 701. The electrochemical biosensor 601 and 709, as chemically constituted, are shown in FIGS. 2-4. Filling of the sample channel slot 701 is detected electronically using the sample volume indicator electrodes 706 and starts the reaction time, after which the flowing faradaic current is read on the detection device 502 as an indication of protease activity in the biological sample 702. If biological sample volume is inadequate, the reaction time is not initiated and electrical meter 502 displays an error message, such as "inadequate sample volume". To eliminate any measurement errors, a new test strip 700 is typically used after an error message.

The chemical reaction to detect protease levels in the biological sample 702 occurs on the electrochemical biosensor 709. Respective embodiments of the electrochemical bionsensor include the PepOliCon electrochemical biosensor 200, the aptamer electrochemical biosensor 300, or the OligoPepOligo electrochemical biosensor 400. The electrochemical biosensor 709 is prepared for use by attaching the reagents described herein. For the example embodiment illustrated in FIG. 2, the peptide-oligonucleotide conjugate (PepOliCon) 202 and the signaling oligonucleotide 205 are mixed together resulting in a binding interaction between their respective complementary DNA sequences. Then, the duplex (PepOliCon 202 bound to signaling oligonucleotide 205) is attached via covalent bonding to the biosensor electrode 206 via their terminal sulfhydryl groups 201.

As shown in FIG. 2, the lifting peptide keeps the redox reporter 204, an example of which is methylene blue, positioned far enough above the biosensor electrode 206 so as not to produce a faradaic current flowing through the biosensor electrode 206 and subsequently the working electrode connection 605 or 708. Once the reagents 202 and 205 are covalently attached on the biosensor electrode 206, the electrochemical biosensor 200 is ready to receive a biological sample. Biological sample is either pipetted manually onto the working electrode 601 if a test strip such as that depicted in FIG. 6 is used, or is gathered automatically over the biosensor working electrode 709 via capillary action into the sample channel slot 701 of test strip 700, which overlays the electrochemical biosensor 709 that includes the reagent duplex PepOliCon 202 bound to signaling oligonucleotide 205. The lifting peptide moiety of the PepOliCon 202 holds the redox reporter 204 above the biosensor electrode 206 in the ready position prior to cleavage of the substrate cleavage sequence by proteases in the biological sample, thereby preventing electrical current from flowing through the working electrode connection 605 or 708 while the biosensor is in the 'ready' configuration.

If proteases are present in the biological sample, the proteases cleave a specific substrate sequence 203 that is a part of the PepOliCon construct; examples of such protease substrate sequences are disclosed herein as SEQ ID NOs: 1-47. Once cleaved, the DNA portion 207 of the PepOliCon construct is released from the lifting effect of the lifting peptide moiety 202 of the PepOliCon such that the redox reporter 204 collides with the surface of the biosensor electrode 206, thereby causing the flow of electrical current. The lifting peptide moiety of the PepOliCon 202, by its molecular structure, acts like a tensioned spring holding the redox reporter 204 above the biosensor electrode 206 surface. Once cleaved, the effect of the lifting tension is lost thereby allowing the redox reporter 204 to bend towards the biosensor electrode 206 surface; the more protease that is present in the biological sample, the more PepOliCon is cleaved on the electrochemical biosensor 200. Therefore, the amount of current flow is directly proportional to how much protease is present in the biological sample.

The lifting mechanism of biosensor 300 is also mediated by a peptide 302, whereas that of biosensor 400 is mediated via a length of double-stranded DNA consisting of portions of reagents 402 and 405.

In each embodiment depicted in FIGS. 2-4, a sample protease-induced hydrolysis at the top of either a lifting peptide or a lifting double-stranded DNA breaks the attachment between either the lifting peptide of biosensors 200 and 300 or the lifting double-stranded DNA of biosensor 400 and the signaling oligonucleotide or signaling aptamer, thereby releasing the distance constraint between the biosensor electrode 206, 306, or 406 and the respective redox reporter 204, 304, or 404 on the signaling oligonucleotide or signaling aptamer, allowing a faradaic current to flow (ΔE). The magnitude increase in the electrochemical potential, measured in a handheld electrical meter, such as electrical meter 502 in FIG. 5, is directly proportional to the proteolytic activity in the biological sample.

This change in the electrochemical potential (ΔE) is controlled by initially imposing distance constraints on the redox reporter 204, 304, or 404, which in the specific examples presented herein and shown in FIGS. 2-4 is methylene blue (MB), and the distance constraints are released by hydrolysis of peptide substrate sequences by target proteases when they are present in the biological sample. Relative to optical biosensors, electrochemical biosensors are more cost effective, more stable, less susceptible to contaminants and non-specific binding, and involve the use of simpler instrumentations for detection. Furthermore, the detection of electrical signals is not affected by factors such as solution turbidity or opacity, which may cloud the detection of optical signals, including fluorescence.

The first exemplary electrochemical biosensor configuration, depicted in FIG. 2, includes two entities: 1) a peptide-oligonucleotide conjugate (PepOliCon) and 2) a signaling oligonucleotide that binds to the oligonucleotide moiety of the PepOliCon via complementary DNA interactions. The PepOliCon 202 depicted in FIG. 2 (a specific example of which is given by SEQ ID NO: 55) itself contains four interworking components that make the present invention work. First, a binding component 201, such as sulfur, at its terminus used to bind or adhere the PepOliCon to the biosensor electrode 206. Second, a lifting peptide sequence that elevates the redox reporter 204 on the adjacent signaling oligonucleotide 205 far enough above the biosensor electrode 206 to prevent current flow. Third, a protease cleavage sequence 203 that is cleaved by proteases present in the biological sample. Lastly, a DNA oligonucleotide 207 binds to a complementary DNA sequence on the signaling oligonucleotide 205.

Similarly, the signaling oligonucleotide 205 contains three interworking components that make the present invention work. First, a binding component 201, such as sulfur, at one of its termini (5' in the example given in SEQ ID NO: 56) is used to bind or adhere the signaling oligonucleotide 205 to the biosensor electrode 206. Second, a sequence that is complementary to the DNA oligonucleotide sequence on the PepOliCon promotes a strong binding interaction between the PepOliCon 202 and the signaling oligonucleotide 205. Third, a redox reporter 204, such as methylene blue, attached to its other terminus (3' in the example given in SEQ ID NO: 56).

The second exemplary electrochemical biosensor 300 depicted in FIG. 3, using an aptamer system, works by a similar process to promote the flow of current once cleavage of the protease recognition sequence 303 by sample proteases has occurred. FIG. 3 shows the aptamer configuration of the electrochemical biosensor of the present invention. This configuration also includes two entities: 1) an aptamer-recognition peptide construct 302 containing an aptamer epitope 307, and 2) a signaling aptamer 305. The aptamer recognition peptide construct 302 (a specific example of which is given by SEQ ID NO: 53) consists of four interworking components that make the present invention work. First, a binding component 301, such as sulfur, at its terminus used to bind or adhere the aptamer recognition peptide construct to the biosensor electrode 306. Second, a lifting peptide sequence that elevates the redox reporter 304 on the adjacent signaling aptamer 305 above the biosensor electrode 306 to prevent current flow. Third, a protease cleavage sequence 303 that, when cleaved by proteases present in the biological sample, releases the constraint of the lifting peptide that had been elevating the redox reporter 304 above the biosensor electrode 306 so as to prevent current from flowing. Fourth, a peptide aptamer epitope sequence 307 specifically recognized by an aptamer with which it forms a tight binding interaction.

The signaling aptamer 305 contains four interworking components that make the present invention work. First, a binding component 301, such as sulfur, at one of its termini (3' in the example given in SEQ ID NO: 57) is used to bind or adhere the signaling aptamer 305 to the biosensor electrode 306. Second, a spacer sequence is long enough to allow the peptide recognition sequence of the aptamer to reach up to the specific peptide sequence 307 on the aptamer recognition peptide construct 302 with which it forms a specific, high-affinity binding interaction. Third, the peptide recognition sequence makes a specific high-affinity binding interaction with the peptide aptamer epitope 307 on aptamer-recognition peptide construct 302. Fourth, a redox reporter 304 such as methylene blue, attached to its other terminus (5' in the example given in SEQ ID NO: 57).

The peptide aptamer epitope/aptamer pair can either be chosen from a commercially available pair (e.g. aptamer APT00536 against a 6× His-tag; or APT00523 against a 15-mer acetylated peptide representing the N-terminal tail of Histone 4; or ATP00390 against amyloid peptide betaA4(1-40); or aptamers ATP00308, ATP00309, ATP00310, ATP00311, or ATP00312 against brain natriuretic peptide Ep1, Ep2, Ep3, EP4 or Ep5 (all available from Creative Biogene), or it can be derived from a unique peptide sequence and a new specific high affinity recognition DNA aptamer produced against it as a unique part of the present invention.

The third exemplary electrochemical biosensor 400 depicted in FIG. 4, which uses an OligoPepOligo system, also works by a mechanism that promotes the flow of current once cleavage of a protease recognition sequence by proteases in a biological sample has occurred. This configuration also includes two entities: 1) an oligonucleotide-peptide-oligonucleotide (OligoPepOligo) conjugate 402, containing a protease cleavage sequence 403, and 2) a signaling oligonucleotide 405. The OligoPepOligo 402 includes four interworking components that make the present invention work. First, a binding component 401, such as sulfur, at one of its termini (3' in the examples given in SEQ ID NOs: 60-61) is used to covalently bind or adhere the OligoPepOligo 402 to the biosensor electrode 406. Second, a DNA sequence binds to a complementary DNA sequence on the signaling oligonucleotide, thereby forming a length of double stranded DNA that serves as part of the mechanism that elevates the redox reporter 404 far enough above the biosensor electrode 406 to prevent current flow. Third, a peptide sequence containing a protease cleavage site 403 is joined to oligonucleotide sequences at both its amino-terminal and carboxyl-terminal ends via highly efficient copper(I)-catalyzed alkyne-azide cycloaddition (CuAAC), or strain-promoted alkyne-azide cycloaddition (SPAAC) "click" chemistry. When the peptide is cleaved by proteases in the biological sample, the lifting constraint of the double stranded DNA that holds the redox reporter 404 above the biosensor electrode 406 is released. Fourth, a second oligonucleotide sequence that binds to a complementary DNA sequence further along the signaling oligonucleotide 405.

The signaling oligonucleotide contains five interworking components that make the present invention work. First, a binding component 401, such as sulfur, at one of its termini (5' in the examples given in SEQ ID NOs: 58-59) is used to bind or adhere the signaling oligonucleotide to the biosensor electrode 406. Second, a DNA sequence binds to a complementary DNA sequence on the OligoPepOligo, thereby forming a length of double stranded DNA that serves as the lifting mechanism that elevates the redox reporter 404 far enough above the biosensor electrode 406 to prevent current flow. Third, a short spacer such as the polythymine sequence seen in the center of both SEQ ID NOs: 58-59 which links the two oligonucleotide regions of the signaling oligonucleotide that each make binding interactions with complementary sequences on the OligoPepOligo. Fourth, the second oligonucleotide sequence that binds to a complementary sequence on the OligoPepOligo. Fifth, a redox reporter 404 such as methylene blue, attached to the other terminus of the signaling oligonucleotide (3' in the examples given in SEQ ID NOs: 58-59).

The exemplary OligoPepOligo electrochemical biosensor 400 depicted in FIG. 4 can be configured such that only the signaling oligonucleotide is covalently attached to the biosensor electrode 406 while the OligoPepOligo does not contain a binding component 401 such as sulfur, but is attached to the biosensor only by its complementary DNA binding interactions to the signaling oligonucleotide. While those skilled in the art can appreciate that both configurations of making this biosensor are possible (i.e. the Oligo-PepOligo conjugate 402 may or may not contain a binding component 401, such as sulfur), the fully covalent architecture significantly improves the stability of this OligoPepOligo biosensor and therefore provides a longer shelf life for a commercial product.

Other important qualities of the present invention include, but are not limited to, the ability to provide accurate quantitation; to be free of interfering mechanisms that could lead to false results; and to have a large dynamic and linear range to be able to provide accurate measurement of wound protease activities that can be highly variable in different biological samples, even within chronic wound fluids. It also measures protease activity and not just protease concentration since proteases can be present in inactive forms in biological samples; is cost effective; easy to use; point-of-care; and has an intuitive readout with the detector signal readout from the electrical meter 502 increasing with increasing protease activity.

Examples of human biological samples containing proteases for which the present invention is applicable include, but are not limited to: blood, lymph, wound fluid, saliva, gingival crevice fluid, nasal discharge, mucus from other membranes, bronchoalveolar lavage, urine, and lacrimal fluid. The present invention is also applicable to other bodily fluids in humans and animals and to biological fluids from other phyla such as the culture or growth media of microorganisms, from insects and other invertebrates, plants, and from water samples. One example of such a fluid would include the measurement of neutrophil elastase activity or other NSPs in gingival crevice fluid. Another example would be the measurement of neutrophil elastase activity or other NSPs in bronchoalveolar lavage. Another example would be the measurement of protease activity within wound fluid. In the embodiments exemplified herein, the present invention provides diagnostics for the detection and quantification of the activities of matrix metalloproteinases (MMPs) and neutrophil serine proteases (NSPs) at the site of a wound.

The simplicity and utility of blood glucose monitors is well recognized as essential to the management of diet and insulin therapy in diabetics. The present invention is as simple and important in the management of the therapy of non-healing (chronic) wounds. Unlike the electrochemical sensing methods used in blood glucose measurement, which are based on solvent reorganization energies and which use redox reporters of ferrocene and osmium, the method of the present invention is based upon stereochemical distance constraints imposed by a lifting peptide or a lifting double-stranded DNA between a redox reporter 204, 304, or 404, such as methylene blue (MB) on the terminus of a signaling oligonucleotide or a signaling aptamer, and the surface of the biosensor electrode 206, 306, or 406.

There are millions of patient visits annually to wound clinics throughout the United States, and globally. In an example embodiment of the present invention, the activity of MMPs will be determined. In another example embodiment, the activity of MMPs in wounds will be determined. During the initial visit of each new patient presenting with a non-healing wound, use of the present invention indicates the level of protease activity in the wound at the point of care (POC), to guide the wound management strategy that is initially adopted for each new wound. The electrical meter 502 of the present invention is a single hand-held device shown in FIG. 5 including a test strip either 600 or 700 shown in FIGS. 6 and 7, inserted into the detection input slot 501 of the hand-held electrical meter 502 that provides results in a digital readout of the wound protease activity. The electrical meter 502 and either test strip 600 or 700 of the present invention is simple for doctors, physician's assistants, nurses, patients, and other persons involved in the medical industry to use.

The detection device 500 operates by inserting test strip 700, for example, into the detection input slot 501 of electrical meter 502, then drawing up a small volume (nanoliters to microliters) of biological sample 702 into the end of test strip 700 that is automatically controlled by capillary action into a sample channel 701 of set dimensions, and waiting approximately ten to fifteen minutes (10-15 min.) for the proteolytic chemistry to occur, after which the electrical meter 502 displays the level of protease activity on the screen. Electrical meter 502 senses whether the correct amount of biological sample 702 has been drawn into the sample channel slot 701 within the spacer 707. Next, electrical meter 502 starts timing the reaction. At the end of the reaction time, approximately ten to fifteen minutes (~10-15 min), which is preset in the detection device, the electrical meter 502 provides a numerical readout of the protease activity.

In an example embodiment, the presence of active infection in a wound is assessed by inserting test strip 700, for example, containing a biosensor for the measurement of NSPs, into a electrical meter 502 that is capable of measuring electrical potentials; drawing a small measured sample of wound fluid into the end of the test strip by capillary action; allowing an incubation time of approximately ten to fifteen minutes (~10-15 min.) for proteolysis and electrochemical potential generation; and representing the proteolytic activity in the biological sample by a digital read-out on the electrical meter 502. The number displayed on electrical meter 502, quantitating the level of NSP protease activity in biological sample 702, is entered into the patient's medical records by the wound care provider as an indication of the level of active infection. In another example embodiment, the activity of NSPs in gingival crevice fluid, using the same methodology, indicates the presence of plaque or tooth biofilm associated with gingivitis and/or periodontitis. In yet another example embodiment, the activity of NSPs in bronchoalveolar lavage indicates the level of protease activity in the lungs that are associated with active infections, irreversible lung tissue degeneration, such as in emphysema and other chronic obstructive pulmonary disease (COPD) in adults, and chronic lung disease (CLD) in infants.

The present invention distinguishes itself from other methods in that it uses a specific signal-on distance-constraining molecular architecture to control the stereochemistry of molecules attached to an electrode surface, such as the biosensor electrodes 206, 306, or 406, to ensure that an electrochemical potential is prevented or minimized prior to the introduction of biological sample. Specifically, the chemical constraint system utilizes lifting peptides or double-stranded DNA in peptide-oligonucleotide (PepOliCon) or oligonucleotide-peptide-oligonucleotide (OligoPepOligo) conjugates, respectively, or lifting peptides conjugated to aptamer epitopes to elevate a redox reporter 204, 304 or 404, such as methylene blue, attached to a signaling oligonucleotide or a signaling aptamer, above the biosensor electrode 206, 306, or 406, until hydrolysis of specific protease cleavage sites incorporated into the biosensor construct by sample proteases. The distance constraints maintaining the redox reporter 204, 304 or 404 out of signal range from the biosensor electrode 206, 306 or 406, respectively are released via enzyme hydrolysis by sample proteases, thereby allowing the redox reporter 204, 304, or 404 to approach the biosensor electrode 206, 306 or 406, respectively and initiate an electrochemical potential through the working electrode connector 605 or 708, which potential is directly proportional to the protease activity present in a biological sample.

Sequences

There are peptide sequences, oligonucleotide sequences, and conjugates of both that are subjects of the present invention, as illustrated in the embodiments shown in FIGS. 2, 3, and 4. Preferred peptide sequences for the present invention are of three kinds: protease cleavage sequences; lifting peptide sequences that help elevate the redox reporter moiety above the electrode in the ready position; and third, either commercially available or unique peptide sequences that are aptamer antigens.

Oligonucleotide sequences important to the present invention are also of three kinds: sequences that are conjugated to peptides (either PepOliCon or OligoPepOligo conjugates) and which are designed to be complementary to portions of sequences on signaling oligonucleotides; signaling oligonucleotides that support a redox reporter and/or a binding component, such as sulfur on their termini and contain complementary sequences to those conjugated to peptides; and specific aptamer sequences with recognition for specific peptides. The first two are deoxyribonucleic acid (DNA) sequences, whereas the third, aptamer-type sequences may also be constituted by ribonucleic acid (RNA) sequences.

Protease Cleavage Sequences

Proteases that contribute to the degradation of extracellular matrix proteins, cytokines, growth factors, and cell surface receptors in wounds include matrix metalloproteinses, MMP-1, MMP-2, MMP-3, MMP-7, MMP-8, MMP-9, and MMP-13. Serine proteases also contribute to tissue degradation, often at sites of infection, and the present invention calls for Neutrophil Serine Proteases (NSPs) to be used as specific indicators of active infection. The primary serine proteases released from neutrophils that are recruited to sites of active infection and which indicate stress of the host are neutrophil elastase (NE), proteinase-3 (Pr3) and cathepsin-G (CG). Examples of substrate sequences used for the present invention include, but are not limited to those that are promiscuous for multiple proteases, or those that are specific, or somewhat discriminatory for individual proteases.

Some examples of each are given below using the single letter designation code for amino acids. The cleavage position in each is indicated by a forward slash.

| PROMISCUOUS MMP SUBSTRATE SEQUENCES |
|---|
| GPQG/IAGQ (SEQ ID NO: 1) |
| GPQG/LAGQ (SEQ ID NO: 2) |
| GPQG/IFGQ (SEQ ID NO: 3) |
| GPQG/IWGQ (SEQ ID NO: 4) |
| GPQG/ILGQ (SEQ ID NO: 5) |
| GPQG/IRGQ (SEQ ID NO: 6) |
| GPQG/IAAQ (SEQ ID NO: 7) |
| GPQG/IAGA (SEQ ID NO: 8) |
| GPQG/IAGH (SEQ ID NO: 9) |
| GPQG/IAGT (SEQ ID NO: 10) |
| GPQA/IAGQ (SEQ ID NO: 11) |
| GPLG/IAGQ (SEQ ID NO: 12) |
| GPYG/IAGQ (SEQ ID NO: 13) |
| FLLE/LIGGPL (SEQ ID NO: 14) |
| MACG/LVASNL (SEQ ID NO: 15) |
| VASN/LNLKPG (SEQ ID NO: 16) |
| SNLN/LKPGE (SEQ ID NO: 17) |
| FVLN/LGKDS (SEQ ID NO: 18) |
| RPVP/QGSCQ (SEQ ID NO: 19) |

-continued

| SUBSTRATE SEQUENCES PROMISCUOUS FOR MMP-2 AND MMP-9 |
|---|
| SGAKPRA/LTAQ (SEQ ID NO: 20) |
| SGESPAY/YTAQ (SEQ ID NO: 21) |
| SGESLRY/YTAQ (SEQ ID NO: 22) |
| SGRSLRR/LTAQ (SEQ ID NO: 23) |
| SGAPSW/LLTA (SEQ ID NO: 24) |
| SGAVRW/LLTA (SEQ ID NO: 25) |

| SUBSTRATE SEQUENCES MORE SPECIFIC FOR MMP-9 |
|---|
| GPLF/YSVQ (SEQ ID NO: 26) |
| KIPRT/LTAQ (SEQ ID NO: 27) |
| GPRT/LTGQ (SEQ ID NO: 28) |
| GPLR/LSWQ (SEQ ID NO: 29) |
| GPRA/VSTQ (SEQ ID NO: 30) |
| KGPRQ/ITAQ (SEQ ID NO: 31) |
| AGSG/LKAQ (SEQ ID NO: 32) |
| GAMG/LKSQ (SEQ ID NO: 33) |
| AGRR/LIHH (SEQ ID NO: 34) |
| GLARN/ITAQ (SEQ ID NO: 35) |
| FGSRY/LTAQ (SEQ ID NO: 36) |

| PROMISCUOUS NSP SUBSTRATE SEQUENCES |
|---|
| GIATFC/MLMPEQ (SEQ ID NO: 37) |
| AAPV/LSAQ (SEQ ID NO: 38) |
| APEEI/MRRQ (SEQ ID NO: 39) |
| GKPV/SLSY (SEQ ID NO: 40) |
| APEEI/MDRQ (SEQ ID NO: 41) |
| YTRV/AEMR (SEQ ID NO: 42) |
| TRVA/EMRG (SEQ ID NO: 43) |
| MESV/CGYF (SEQ ID NO: 44) |

| SUBSTRATE SEQUENCES MORE SPECIFIC FOR NE |
|---|
| ▬▬ Nle(O-Bzl)-Met(O₂)-Oic-Abu/LSAQ (SEQ ID NO: 45) ■ ■ ■ ■ ■ ■ ■ |
| Nle(O-Bzl) = 6-benzyl-norcleucine<br>Met(O₂) = methionine dioxide<br>Oic = octahydro-1H-indole-2-carboxylic acid<br>Abu = aminobutyric acid |
| SUBSTRATE SEQUENCES PROMISCUOUS FOR MMPS AND NSPS |
| ▬▬ GPQG/IFGQ-GIATFC/MLMPEQ (SEQ ID NO: 46) ■ ■ ■ ■ ■ ■ ■ |
| ▬▬ GPQG/IFGQ-AAPV/LSAQ (SEQ ID NO: 47) ■ ■ ■ ■ ■ ■ ■ |

In the above sequences, the solid black line on the left of each represents a lifting peptide sequence (such as SEQ ID NOs: 48-50) or an oligonucleotide sequence that forms a double stranded DNA structure with a complementary sequence in another oligonucleotide construct (such as sequences contained within SEQ ID NOs: 58-59 form double-stranded DNA with complementary sequences contained within SEQ ID NOs: 60-61), either of which mechanism contributes to the elevation of the redox reporter above the biosensor electrode 206, 306, or 406 surface in the ready configuration where the redox reporter 204, 304, or 404, respectively, cannot cause a faradaic current to flow through the biosensor electrode 206, 306, or 406. In the above SEQ ID NOs: 1-47, the dashed black line on the right of each sequence represents oligonucleotide sequences (such as SEQ ID NO: 54), which are complementary to sequences in signaling oligonucleotides (such as that in SEQ ID NO: 56). The entire constructs are known as either peptide-oligonucleotide conjugate (PepOliCon; an example of which is SEQ ID NO: 55) or oligonucleotide-peptide-oligonucleotide (OligoPepOligo) sequences (examples of which are SEQ ID NOs: 60 & 61). In the literature, peptide-oligonucleotide conjugate sequences are abbreviated as POC, but within the field of the present invention the abbreviation 'POC' is restricted to designate Point-of-Care, and herein peptide-oligonucleotide conjugate is abbreviated as PepOliCon.

Examples of lifting peptide sequences include, but are not limited to the following.

CEELRVRLASHLRKLRKRL (SEQ ID NO: 48). The de novo peptide structure prediction program known as PEP-FOLD, predicts that this peptide will adopt an α-helical structure that would be suitable as a lifting peptide in the present invention. Within its native apolipoprotein E structure this sequence also exists as an α-helix. The predicted elongated lifting structure of this peptide, with promiscuous MMP substrate (SEQ ID NO: 3) attached to its carboxyl-terminus (i.e. the sequence depicted as SEQ ID NO: 51) is indicated in FIG. 1.

CVLVLVLVL (SEQ ID NO: 49). The de novo peptide structure prediction program known as PEP-FOLD predicts that this peptide will adopt an elongated structure that would be suitable as a lifting peptide in the present invention.

DDAADDSADC (SEQ ID NO: 50). The de novo peptide structure prediction program known as PEP-FOLD predicts that this peptide will adopt an elongated structure that would be suitable as a lifting peptide in the present invention.

An example of a peptide sequence that includes a lifting peptide with a protease substrate sequence attached at the terminus that would be elevated above the biosensor electrode 206 or 306 includes, but is not limited to the following.

CEELRVRLASHLRKLRKRL-GPQG/IFGQ (SEQ ID NO: 51). The predicted structure of SEQ ID NO: 51, composed of lifting peptide SEQ ID NO: 48 with promiscuous MMP substrate SEQ ID NO: 3 joined at its carboxyl-terminus is shown in FIG. 1.

CVLVLVLVL-GIATFC/MLMPEQ (SEQ ID NO: 52). This peptide is composed of lifting peptide SEQ ID NO: 49 with promiscuous NSP substrate SEQ ID NO: 37 joined at its carboxyl-terminus.

An example of a polypeptide sequence consisting of a lifting peptide sequence, followed by a protease substrate sequence and then a specific aptamer recognition sequence (aptamer epitope; in this case the Histone 4-K16(Ac) N-terminal tail) includes, but is not limited to the following:

OLIGONUCLEOTIDE SEQUENCES
(SEQ ID NO: 53)
CEELRVRLASHLRKLRKRL-GPQG/IFGQ-GGKGLGKGGAK(Ac)RHRK

Examples of DNA oligonucleotide sequences include, but are not limited to, the following.

(a) DNA sequence that binds to a complementary DNA sequence in another oligonucleotide sequence and which can be conjugated to lifting peptides in PepOliCons, or peptides constituting protease cleavage sites in OligoPepOligos.

(SEQ ID NO: 54)
5'-CCATCTCCACTGC-3'

(b) example of a fully conjugated peptide-oligonucleotide (PepOliCon). [For clarity, in the PepOliCon and OligoPepOligo conjugate sequences, amino acids are depicted using their conventional three-letter code and nucleic acids are depicted using their conventional single-letter codes].

(SEQ ID NO: 55)
Cys-Glu-Glu-Leu-Arg-Val-Arg-Leu-Ala-Ser-His-Leu-
Arg-Lys-Leu-Arg-Lys-Arg-Leu-Gly-Pro-Gln-Gly/Ile-
Phe-Gly-Gln-Lys(N₃)-5'hexynyl-CCATCTCCACTGC-3'

(c) signaling oligonucleotide to be used in the PepOliCon Biosensor configuration.

(SEQ ID NO: 56)
3'-MB-(CH₂)₂-C-GGTAGAGGTGACG-TTGGGTGTTGTGTCCAACCC-
(CH₂)₆-S-S-(CH₂)₆-5'

(d) signaling oligonucleotide aptamer sequence (includes Histone 4-K16(Ac) N-terminal tail aptamer)

(SEQ ID NO: 57)
5'-MB-(CH$_2$)$_2$-C-GTAAGTTAATTGGACTTGGTCGTGTGCGGCACAGC
GAT-TTGGGTGTTGTGTCCAACCC-(CH$_2$)$_6$-S-S-(CH$_2$)$_6$-3'

(e) signaling oligonucleotides to be used in the Oligo-PepOligo Biosensor configuration.

(SEQ ID NO: 58)
5'-SH-(CH$_2$)$_6$-CCATCTCCACTC-GTTTTT-CGTGCTTCTG-
(CH$_2$)$_2$-MB-3'

(SEQ ID NO: 59)
5'-SH-(CH$_2$)$_6$-CGTGCTTCTGCT-GTTTTT-CCATCTCCAC-
(CH$_2$)$_2$-MB-3'

(f) oligonucleotide-peptide-oligonucleotide (OligoPepOligo) sequences (SEQ ID NO: 60)
3'-SH-(CH$_2$)$_6$-GGTAGAGGTGAG-TriazoleLinker1-Gly-
Pro-Gln-Gly/Ile-Phe-Gly-Gln-TriazolLinker2-
GCACGAAGAC-T-5'

(SEQ ID NO: 61)
3'-SH-(CH$_2$)$_6$-GCACGAAGACGA-TriazoleLinker1-Ala-
Ala-Pro-Val/Leu-Ser-Ala-Gln-TriazoleLinker2-
GGTAGAGGTG-T-5'

Peptide-oligonucleotide (PepOliCon) and oligonucleotide-peptide-oligonucleotide (OligoPepOligo) conjugates can be produced by the highly efficient copper(I)-catalyzed alkyne-azide cyloaddition (CuAAC) or Strain-Promoted Alkyne-Azide Cycloaddition (SPAAC) "click" chemistry. CuAAC conjugation is efficient for azido-modification of amines at either the 3'-end or the 5'-end of an oligonucleotide. A second oligonucleotide modification approach, specific to the 5'-terminus consists of adding 5'-bromohexyl phosphoramidite in the last synthesis cycle. This modifier can then be easily transformed into a 5'-azido group by displacement of bromide using sodium azide. The first method can be performed in solution while the other allows the azide addition to be performed in solid phase on the synthesis column prior to cleavage and deprotection of the oligonucleotide. If the oligonucleotide is derivatized with azide, the peptide moiety is derivatized with alkyne, for example by alkyne-activated ester. Peptides can also be derivatized at either the amino- or carboxyl-terminal end by azide, and in that case alkyne-containing oligonucleotide can be prepared with alkyne phosphoramidite.

Copper-free "click" chemistry is also available. In this case, the oligonucleotide entity is terminally labeled with a cyclooctyne compound (such as DBCO or BCN) and the peptide binding partner is labeled with azide. The reaction of these partners is known as strain-promoted alkyne-azide cycloaddition (SPAAC), and results in a cross-linked triazole conjugate. Diarylcyclooctynes are thermostabile with very narrow and specific reactivity towards azides, resulting in almost quantitative yields of stable triazoles. The use of the strained cyclooctyne decreases the activation energy for the cycloaddition "click" reaction, enabling it to be carried out without the need for catalysis at low temperatures with an efficiency greater than that of the Cu(I)-catalyzed ligation. In another rendition of the "click" chemistry, conjugation can also be effected by inclusion of a cysteine at the peptide terminus to be conjugated using succinimidyl ester linkage, such as SMCC with a C6 amino linkage that binds to the oligonucleotide terminus.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

What is claimed is:

1. A method for detecting proteases, which comprises:

providing an electrochemical biosensor, said electrochemical biosensor including:

a biosensor electrode;

a first reagent including:

a lifting structure having a first terminus and a second terminus, said first terminus opposing said second terminus, said first terminus being covalently bonded to said biosensor electrode;

a protease substrate peptide sequence having a first terminus and a second terminus, said first terminus opposing said second terminus, said first terminus being connected to said second terminus of said lifting structure; and a first binding component being connected to said second terminus of said protease substrate sequence;

a second reagent known as a signaling oligonucleotide including:

a spacer sequence having a first terminus and a second terminus, said first terminus opposing said second terminus, said first terminus being covalently bonded to said biosensor electrode;

a second binding component having a first terminus and a second terminus, said first terminus opposing said second terminus, said first terminus being connected to said second terminus of said spacer sequence, said second binding component being specifically bound to said first binding component on said first reagent; and a redox reporter being connected to said second terminus of said second binding component;

said lifting structure being connected to said first binding component before said protease substrate sequence is cleaved;

said lifting structure imposing a distance constraint between said redox reporter and said biosensor electrode before said protease substrate sequence is cleaved;

said protease substrate sequence being cleavable by a protease; and said redox reporter contacting said biosensor electrode when said protease substrate sequence is cleaved;

applying a sample to said electrochemical biosensor; and detecting an electrical change across said biosensor electrode, wherein the detecting step occurs within fifteen minutes (≤15 min) after the sample is applied to said biosensor electrode.

2. The method according to claim 1, wherein:
said lifting structure includes a peptide; and
said first binding component includes an oligonucleotide.

3. The method according to claim 1, wherein:
said lifting structure includes a peptide;
said first binding component of said first reagent is an aptamer-recognition peptide sequence; and
said second binding component of said second reagent is an aptamer sequence.

4. The method according to claim 1, wherein:
said lifting structure includes a first double-stranded DNA segment;
a first strand of said first double-stranded DNA segment includes a portion of said first reagent;
a second strand of said first double-stranded DNA segment includes a portion of said second reagent;
said first binding component of said first reagent is a first strand of a second double-stranded DNA segment; and
said second binding component of said second reagent is a second strand of said second double-stranded DNA segment.

5. The method according to claim 1, wherein said protease cleavage sequence is an MMP substrate sequence selected from the group consisting of SEQ ID NOs: 1-36.

6. The method according to claim 1, wherein said protease cleavage sequence is an NSP substrate sequence selected from the group consisting of SEQ ID NOs: 37-45.

7. The method according to claim 1, wherein said protease cleavage sequence includes an MMP substrate sequence and an NSP substrate sequence selected from the group consisting of SEQ ID NOs: 46-47.

8. The method according to claim 1, wherein said lifting structure is a peptide selected from the group consisting of SEQ ID NOs: 48-50.

9. The method according to claim 4, wherein said first strand of said first double-stranded DNA sequence includes a sequence selected from the group consisting of SEQ ID NOs: 58-59 and said second strand of said second double-stranded DNA sequence selected from the group consisting of SEQ ID NOs: 60-61, respectively (noting that SEQ ID NO: 60 incorporates SEQ ID NO: 63 at the 3'-end and SEQ ID NO: 64 at the 5'-end; and, that SEQ ID NO: 61 incorporates SEQ ID NO: 65 at the 3'-end and SEQ ID NO: 66 at the 5'-end).

10. The method according to claim 1, wherein said signaling oligonucleotide is selected from the group consisting of SEQ ID NOs: 56-59.

11. The method according to claim 1, wherein said first reagent and said second reagent are bound to each other via complementary oligonucleotide sequences and are composed of a peptide-oligonucleotide conjugate described in SEQ ID NO: 55, said SEQ ID NO. 55 being constituted by SEQ ID NO: 51 and conjugated to SEQ ID NO: 54, and signaling oligonucleotide SEQ ID NO: 56 (noting that SEQ ID NO: 55 incorporates attachment of SEQ ID NO: 62 at the carboxy-terminus).

12. The method according to claim 1, wherein said first reagent and said second reagent are bound to each other via complementary oligonucleotide sequences and are composed of a peptide-oligonucleotide conjugate described in SEQ ID NO: 55, said SEQ ID NO. 55 being constituted by conjugating SEQ ID NO: 52 and SEQ ID NO: 54, and signaling oligonucleotide SEQ ID NO: 56 (noting that SEQ ID NO: 55 incorporates attachment of SEQ ID NO: 62 at the carboxy-terminus).

13. The method according to claim 1, wherein said first reagent and said second reagent are bound to each other via aptamer recognition peptide/aptamer interaction and are composed of an aptamer recognition peptide described in SEQ ID NO: 53 and a signaling oligonucleotide aptamer described in SEQ ID NO: 57.

14. The method according to claim 1, wherein said first reagent and said second reagent are composed of said oligonucleotide-peptide-oligonucleotide conjugates and are selected from the group consisting of SEQ ID NOs: 60-61 and said signaling oligonucleotides selected from the group consisting of SEQ ID NOs: 58-59, respectively (noting that SEQ ID NO: 60 incorporates SEQ ID NO: 63 at the 3'-end and SEQ ID NO: 64 at the 5'-end; and, that SEQ ID NO: 61 incorporates SEQ ID NO: 65 at the 3'-end and SEQ ID NO: 66 at the 5'-end).

15. The method according to claim 1, wherein said the redox reporter is methylene blue.

16. The method according to claim 1, wherein said biosensor electrode is made of a material selected from the group consisting of gold, platinum, carbon, nafion-coated carbon, and polymers thereof.

17. The method according to claim 1, which further comprises taking said sample from a site selected from the group consisting of a wound, gingival crevice fluid, and bronchoalveolar lavage.

18. The method according to claim 1, wherein said proteases are active MMP or NSP proteases that indicate abnormally elevated protease levels, and/or an active infection.

* * * * *

SEQUENCE LISTING

```
<160> NUMBER OF SEQ ID NOS: 66

<210> SEQ ID NO 1
<211> LENGTH: 8
<212> TYPE: PRT
<213> ORGANISM: Homo sapiens
<220> FEATURE:
<221> NAME/KEY: Collagen Alpha-1(I) Chain (1464 aa)
<222> LOCATION: FROM 950 TO 957
<223> OTHER INFORMATION: Residues P4 to P4 Prime
<300> PUBLICATION INFORMATION:
<308> DATABASE ACCESSION NUMBER: UniProtKB P02452

<400> SEQUENCE: 1

Gly Pro Gln Gly Ile Ala Gly Gln
1               5

<210> SEQ ID NO 2
<211> LENGTH: 8
<212> TYPE: PRT
<213> ORGANISM: Homo sapiens
<220> FEATURE:
<221> NAME/KEY: Collagen Alpha-1(I) Chain
<222> LOCATION: FROM 950 TO 957
<223> OTHER INFORMATION: Residues P4 to P4 Prime
<220> FEATURE:
```

<223> OTHER INFORMATION: P1 Prime substitution from Ile to Leu
<300> PUBLICATION INFORMATION:
<308> DATABASE ACCESSION NUMBER: UniProtKB P02452
<300> PUBLICATION INFORMATION:
<301> AUTHORS: Nagase, Hideaki
<302> TITLE: Substrate Specificity of MMPs
<303> JOURNAL: Matrix Metalloproteinase Inhibitors in Cancer Therapy.
      Eds: Clendininn NJ, Appelt K. Humana Press, Totowa,
      New Jersey
<306> PAGES: 39-66
<307> DATE: 2001

<400> SEQUENCE: 2

Gly Pro Gln Gly Leu Ala Gly Gln
1               5

<210> SEQ ID NO 3
<211> LENGTH: 8
<212> TYPE: PRT
<213> ORGANISM: Homo sapiens
<220> FEATURE:
<221> NAME/KEY: Collagen Alpha-1(I) Chain
<222> LOCATION: FROM 950 TO 957
<223> OTHER INFORMATION: Residues P4 to P4 Prime
<220> FEATURE:
<223> OTHER INFORMATION: P2 Prime substitution from Ala to Phe
<300> PUBLICATION INFORMATION:
<308> DATABASE ACCESSION NUMBER: UniProtKB P02452
<300> PUBLICATION INFORMATION:
<301> AUTHORS: Nagase, Hideaki
<302> TITLE: Substrate Specificity of MMPs
<303> JOURNAL: Matrix Metalloproteinase Inhibitors in Cancer Therapy.
      Eds: Clendininn NJ, Appelt K. Humana Press, Totowa,
      New Jersey
<306> PAGES: 39-66
<307> DATE: 2001

<400> SEQUENCE: 3

Gly Pro Gln Gly Ile Phe Gly Gln
1               5

<210> SEQ ID NO 4
<211> LENGTH: 8
<212> TYPE: PRT
<213> ORGANISM: Homo sapiens
<220> FEATURE:
<221> NAME/KEY: Collagen Alpha-1(I) Chain
<222> LOCATION: FROM 950 TO 957
<223> OTHER INFORMATION: Residues P4 to P4 Prime
<220> FEATURE:
<223> OTHER INFORMATION: P2 Prime substitution from Ala to Trp
<300> PUBLICATION INFORMATION:
<308> DATABASE ACCESSION NUMBER: UniProtKB P02452
<300> PUBLICATION INFORMATION:
<301> AUTHORS: Nagase, Hideaki
<302> TITLE: Substrate Specificity of MMPs
<303> JOURNAL: Matrix Metalloproteinase Inhibitors in Cancer Therapy.
      Eds: Clendininn NJ, Appelt K. Humana Press, Totowa,
      New Jersey
<306> PAGES: 39-66
<307> DATE: 2001

<400> SEQUENCE: 4

Gly Pro Gln Gly Ile Trp Gly Gln
1               5

<210> SEQ ID NO 5
<211> LENGTH: 8
<212> TYPE: PRT
<213> ORGANISM: Homo sapiens
<220> FEATURE:
<221> NAME/KEY: Collagen Alpha-1(I) Chain
<222> LOCATION: FROM 950 TO 957

```
<223> OTHER INFORMATION: Residues P4 to P4 Prime
<220> FEATURE:
<223> OTHER INFORMATION: P2 Prime substitution from Ala to Leu
<300> PUBLICATION INFORMATION:
<308> DATABASE ACCESSION NUMBER: UniProtKB P02452
<300> PUBLICATION INFORMATION:
<301> AUTHORS: Nagase, Hideaki
<302> TITLE: Substrate Specificity of MMPs
<303> JOURNAL: Matrix Metalloproteinase Inhibitors in Cancer Therapy.
      Eds: Clendininn NJ, Appelt K. Humana Press, Totowa,
      New Jersey
<306> PAGES: 39-66
<307> DATE: 2001

<400> SEQUENCE: 5

Gly Pro Gln Gly Ile Leu Gly Gln
1               5

<210> SEQ ID NO 6
<211> LENGTH: 8
<212> TYPE: PRT
<213> ORGANISM: Homo sapiens
<220> FEATURE:
<221> NAME/KEY: Collagen Alpha-1(I) Chain
<222> LOCATION: FROM 950 TO 957
<223> OTHER INFORMATION: Residues P4 to P4 Prime
<220> FEATURE:
<223> OTHER INFORMATION: P2 Prime substitution from Ala to Arg
<300> PUBLICATION INFORMATION:
<308> DATABASE ACCESSION NUMBER: UniProtKB P02452
<300> PUBLICATION INFORMATION:
<301> AUTHORS: Nagase, Hideaki
<302> TITLE: Substrate Specificity of MMPs
<303> JOURNAL: Matrix Metalloproteinase Inhibitors in Cancer Therapy.
      Eds: Clendininn NJ, Appelt K. Humana Press, Totowa,
      New Jersey
<306> PAGES: 39-66
<307> DATE: 2001

<400> SEQUENCE: 6

Gly Pro Gln Gly Ile Arg Gly Gln
1               5

<210> SEQ ID NO 7
<211> LENGTH: 8
<212> TYPE: PRT
<213> ORGANISM: Homo sapiens
<220> FEATURE:
<221> NAME/KEY: Collagen Alpha-1(I) Chain
<222> LOCATION: FROM 950 TO 957
<223> OTHER INFORMATION: Residues P4 to P4 Prime
<220> FEATURE:
<223> OTHER INFORMATION: P3 Prime substitution from Gly to Ala
<300> PUBLICATION INFORMATION:
<308> DATABASE ACCESSION NUMBER: UniProtKB P02452
<300> PUBLICATION INFORMATION:
<301> AUTHORS: Nagase, Hideaki
<302> TITLE: Substrate Specificity of MMPs
<303> JOURNAL: Matrix Metalloproteinase Inhibitors in Cancer Therapy.
      Eds: Clendininn NJ, Appelt K. Humana Press, Totowa,
      New Jersey
<306> PAGES: 39-66
<307> DATE: 2001

<400> SEQUENCE: 7

Gly Pro Gln Gly Ile Ala Ala Gln
1               5

<210> SEQ ID NO 8
<211> LENGTH: 8
<212> TYPE: PRT
<213> ORGANISM: Homo sapiens
<220> FEATURE:
```

```
<221> NAME/KEY: Collagen Alpha-1(I) Chain
<222> LOCATION: FROM 950 TO 957
<223> OTHER INFORMATION: Residues P4 to P4 Prime
<220> FEATURE:
<223> OTHER INFORMATION: P4 Prime substitution from Gln to Ala
<300> PUBLICATION INFORMATION:
<308> DATABASE ACCESSION NUMBER: UniProtKB P02452
<300> PUBLICATION INFORMATION:
<301> AUTHORS: Nagase, Hideaki
<302> TITLE: Substrate Specificity of MMPs
<303> JOURNAL: Matrix Metalloproteinase Inhibitors in Cancer Therapy.
      Eds: Clendininn NJ, Appelt K. Humana Press, Totowa,
      New Jersey
<306> PAGES: 39-66
<307> DATE: 2001

<400> SEQUENCE: 8

Gly Pro Gln Gly Ile Ala Gly Ala
1               5

<210> SEQ ID NO 9
<211> LENGTH: 8
<212> TYPE: PRT
<213> ORGANISM: Homo sapiens
<220> FEATURE:
<221> NAME/KEY: Collagen Alpha-1(I) Chain
<222> LOCATION: FROM 950 TO 957
<223> OTHER INFORMATION: Residues P4 to P4 Prime
<220> FEATURE:
<223> OTHER INFORMATION: P4 Prime substitution from Gln to His
<300> PUBLICATION INFORMATION:
<308> DATABASE ACCESSION NUMBER: UniProtKB P02452
<300> PUBLICATION INFORMATION:
<301> AUTHORS: Nagase, Hideaki
<302> TITLE: Substrate Specificity of MMPs
<303> JOURNAL: Matrix Metalloproteinase Inhibitors in Cancer Therapy.
      Eds: Clendininn NJ, Appelt K. Humana Press, Totowa,
      New Jersey
<306> PAGES: 39-66
<307> DATE: 2001

<400> SEQUENCE: 9

Gly Pro Gln Gly Ile Ala Gly His
1               5

<210> SEQ ID NO 10
<211> LENGTH: 8
<212> TYPE: PRT
<213> ORGANISM: Homo sapiens
<220> FEATURE:
<221> NAME/KEY: Collagen Alpha-1(I) Chain
<222> LOCATION: FROM 950 TO 957
<223> OTHER INFORMATION: Residues P4 to P4 Prime
<220> FEATURE:
<223> OTHER INFORMATION: P4 Prime substitution from Gln to Thr
<300> PUBLICATION INFORMATION:
<308> DATABASE ACCESSION NUMBER: UniProtKB P02452
<300> PUBLICATION INFORMATION:
<301> AUTHORS: Nagase, Hideaki
<302> TITLE: Substrate Specificity of MMPs
<303> JOURNAL: Matrix Metalloproteinase Inhibitors in Cancer Therapy.
      Eds: Clendininn NJ, Appelt K. Humana Press, Totowa,
      New Jersey
<306> PAGES: 39-66
<307> DATE: 2001

<400> SEQUENCE: 10

Gly Pro Gln Gly Ile Ala Gly Thr
1               5

<210> SEQ ID NO 11
<211> LENGTH: 8
<212> TYPE: PRT
```

```
<213> ORGANISM: Homo sapiens
<220> FEATURE:
<221> NAME/KEY: Collagen Alpha-1(I) Chain
<222> LOCATION: FROM 950 TO 957
<223> OTHER INFORMATION: Residues P4 to P4 Prime
<220> FEATURE:
<223> OTHER INFORMATION: P1 substitution from Gly to Ala
<300> PUBLICATION INFORMATION:
<308> DATABASE ACCESSION NUMBER: UniProtKB P02452
<300> PUBLICATION INFORMATION:
<301> AUTHORS: Nagase, Hideaki
<302> TITLE: Substrate Specificity of MMPs
<303> JOURNAL: Matrix Metalloproteinase Inhibitors in Cancer Therapy.
      Eds: Clendininn NJ, Appelt K. Humana Press, Totowa,
      New Jersey
<306> PAGES: 39-66
<307> DATE: 2001

<400> SEQUENCE: 11

Gly Pro Gln Ala Ile Ala Gly Gln
1               5

<210> SEQ ID NO 12
<211> LENGTH: 8
<212> TYPE: PRT
<213> ORGANISM: Homo sapiens
<220> FEATURE:
<221> NAME/KEY: Collagen Alpha-1(I) Chain
<222> LOCATION: FROM 950 TO 957
<223> OTHER INFORMATION: Residues P4 to P4 Prime
<220> FEATURE:
<223> OTHER INFORMATION: P2 substitution from Gln to Leu
<300> PUBLICATION INFORMATION:
<308> DATABASE ACCESSION NUMBER: UniProtKB P02452
<300> PUBLICATION INFORMATION:
<301> AUTHORS: Nagase, Hideaki
<302> TITLE: Substrate Specificity of MMPs
<303> JOURNAL: Matrix Metalloproteinase Inhibitors in Cancer Therapy.
      Eds: Clendininn NJ, Appelt K. Humana Press, Totowa,
      New Jersey
<306> PAGES: 39-66
<307> DATE: 2001

<400> SEQUENCE: 12

Gly Pro Leu Gly Ile Ala Gly Gln
1               5

<210> SEQ ID NO 13
<211> LENGTH: 8
<212> TYPE: PRT
<213> ORGANISM: Homo sapiens
<220> FEATURE:
<221> NAME/KEY: Collagen Alpha-1(I) Chain
<222> LOCATION: FROM 950 TO 957
<223> OTHER INFORMATION: Residues P4 to P4 Prime
<220> FEATURE:
<223> OTHER INFORMATION: P2 substitution from Gln to Tyr
<300> PUBLICATION INFORMATION:
<308> DATABASE ACCESSION NUMBER: UniProtKB P02452
<300> PUBLICATION INFORMATION:
<301> AUTHORS: Nagase, Hideaki
<302> TITLE: Substrate Specificity of MMPs
<303> JOURNAL: Matrix Metalloproteinase Inhibitors in Cancer Therapy.
      Eds: Clendininn NJ, Appelt K. Humana Press, Totowa,
      New Jersey
<306> PAGES: 39-66
<307> DATE: 2001

<400> SEQUENCE: 13

Gly Pro Tyr Gly Ile Ala Gly Gln
1               5

<210> SEQ ID NO 14
```

```
<211> LENGTH: 10
<212> TYPE: PRT
<213> ORGANISM: Artificial Sequence
<220> FEATURE:
<223> OTHER INFORMATION: Protease Cleavage Sequence

<400> SEQUENCE: 14

Phe Leu Leu Glu Leu Ile Gly Gly Pro Leu
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Protease Cleavage Sequence

<400> SEQUENCE: 15

Met Ala Cys Gly Leu Val Ala Ser Asn Leu
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Protease Cleavage Sequence

<400> SEQUENCE: 16

Val Ala Ser Asn Leu Asn Leu Lys Pro Gly
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Protease Cleavage Sequence

<400> SEQUENCE: 17

Ser Asn Leu Asn Leu Lys Pro Gly Glu
1               5

<210> SEQ ID NO 18
<211> LENGTH: 9
<212> TYPE: PRT
<213> ORGANISM: Artificial Sequence
<220> FEATURE:
<223> OTHER INFORMATION: Protease Cleavage Sequence

<400> SEQUENCE: 18

Phe Val Leu Asn Leu Gly Lys Asp Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Protease Cleavage Sequence

<400> SEQUENCE: 19

Arg Pro Val Pro Gln Gly Ser Cys Gln
1               5

<210> SEQ ID NO 20
<211> LENGTH: 11
```

```
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-2 Incubation
<300> PUBLICATION INFORMATION:
<301> AUTHORS: Chen, Emily I
      Kridel, Steven J
      Howard, Eric W
      Li, Weizhong
      Godzik, Adam
      Smith, Jeffrey W
<302> TITLE: A Unique Substrate Recognition Profile For Matrix
      Metalloproteinase-2
<303> JOURNAL: The Journal of Biological Chemistry
<304> VOLUME: 277
<305> ISSUE: 6
<306> PAGES: 4485-4491
<307> DATE: 2002

<400> SEQUENCE: 20

Ser Gly Ala Lys Pro Arg Ala Leu Thr Ala Gln
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-2 Incubation
<300> PUBLICATION INFORMATION:
<301> AUTHORS: Chen, Emily I
      Kridel, Steven J
      Howard, Eric W
      Li, Weizhong
      Godzik, Adam
      Smith, Jeffrey W
<302> TITLE: A Unique Substrate Recognition Profile For Matrix
      Metalloproteinase-2
<303> JOURNAL: The Journal of Biological Chemistry
<304> VOLUME: 277
<305> ISSUE: 6
<306> PAGES: 4485-4491
<307> DATE: 2002

<400> SEQUENCE: 21

Ser Gly Glu Ser Pro Ala Tyr Tyr Thr Ala Gln
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-2 Incubation
<300> PUBLICATION INFORMATION:
<301> AUTHORS: Chen, Emily I
      Kridel, Steven J
      Howard, Eric W
      Li, Weizhong
      Godzik, Adam
      Smith, Jeffrey W
<302> TITLE: A Unique Substrate Recognition Profile For Matrix
      Metalloproteinase-2
<303> JOURNAL: The Journal of Biological Chemistry
<304> VOLUME: 277
<305> ISSUE: 6
<306> PAGES: 4485-4491
<307> DATE: 2002

<400> SEQUENCE: 22

Ser Gly Glu Ser Leu Arg Tyr Tyr Thr Ala Gln
```

```
1               5                   10
```

<210> SEQ ID NO 23
<211> LENGTH: 11
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-2 Incubation
<300> PUBLICATION INFORMATION:
<301> AUTHORS: Chen, Emily I
      Kridel, Steven J
      Howard, Eric W
      Li, Weizhong
      Godzik, Adam
      Smith, Jeffrey W
<302> TITLE: A Unique Substrate Recognition Profile For Matrix
      Metalloproteinase-2
<303> JOURNAL: The Journal of Biological Chemistry
<304> VOLUME: 277
<305> ISSUE: 6
<306> PAGES: 4485-4491
<307> DATE: 2002

<400> SEQUENCE: 23

```
Ser Gly Arg Ser Leu Arg Arg Leu Thr Ala Gln
1               5                   10
```

<210> SEQ ID NO 24
<211> LENGTH: 10
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-2 Incubation
<300> PUBLICATION INFORMATION:
<301> AUTHORS: Chen, Emily I
      Kridel, Steven J
      Howard, Eric W
      Li, Weizhong
      Godzik, Adam
      Smith, Jeffrey W
<302> TITLE: A Unique Substrate Recognition Profile For Matrix
      Metalloproteinase-2
<303> JOURNAL: The Journal of Biological Chemistry
<304> VOLUME: 277
<305> ISSUE: 6
<306> PAGES: 4485-4491
<307> DATE: 2002

<400> SEQUENCE: 24

```
Ser Gly Ala Pro Ser Trp Leu Leu Thr Ala
1               5                   10
```

<210> SEQ ID NO 25
<211> LENGTH: 10
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-2 Incubation
<300> PUBLICATION INFORMATION:
<301> AUTHORS: Chen, Emily I
      Kridel, Steven J
      Howard, Eric W
      Li, Weizhong
      Godzik, Adam
      Smith, Jeffrey W
<302> TITLE: A Unique Substrate Recognition Profile For Matrix
      Metalloproteinase-2
<303> JOURNAL: The Journal of Biological Chemistry
<304> VOLUME: 277
<305> ISSUE: 6
<306> PAGES: 4485-4491

```
<307> DATE: 2002

<400> SEQUENCE: 25

Ser Gly Ala Val Arg Trp Leu Leu Thr Ala
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-9 Incubation
<300> PUBLICATION INFORMATION:
<301> AUTHORS: Kridel, Steven J
               Chen, Emily
               Kotra, Lakshmi P
               Howard, Eric W
               Mobashery, Shahriar
               Smith, Jeffrey W
<302> TITLE: Substrate Hydrolysis By Matrix Metalloproteinase-9
<303> JOURNAL: The Journal of Biological Chemistry
<304> VOLUME: 276
<305> ISSUE: 23
<306> PAGES: 20572-20578
<307> DATE: 2001

<400> SEQUENCE: 26

Gly Pro Leu Phe Tyr Ser Val Gln
1               5

<210> SEQ ID NO 27
<211> LENGTH: 9
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-9 Incubation
<300> PUBLICATION INFORMATION:
<301> AUTHORS: Kridel, Steven J
               Chen, Emily
               Kotra, Lakshmi P
               Howard, Eric W
               Mobashery, Shahriar
               Smith, Jeffrey W
<302> TITLE: Substrate Hydrolysis By Matrix Metalloproteinase-9
<303> JOURNAL: The Journal of Biological Chemistry
<304> VOLUME: 276
<305> ISSUE: 23
<306> PAGES: 20572-20578
<307> DATE: 2001

<400> SEQUENCE: 27

Lys Ile Pro Arg Thr Leu Thr Ala Gln
1               5

<210> SEQ ID NO 28
<211> LENGTH: 8
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-9 Incubation
<300> PUBLICATION INFORMATION:
<301> AUTHORS: Kridel, Steven J
               Chen, Emily
               Kotra, Lakshmi P
               Howard, Eric W
               Mobashery, Shahriar
               Smith, Jeffrey W
<302> TITLE: Substrate Hydrolysis By Matrix Metalloproteinase-9
<303> JOURNAL: The Journal of Biological Chemistry
<304> VOLUME: 276
```

```
<305> ISSUE: 23
<306> PAGES: 20572-20578
<307> DATE: 2001

<400> SEQUENCE: 28

Gly Pro Arg Thr Leu Thr Gly Gln
1               5

<210> SEQ ID NO 29
<211> LENGTH: 8
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-9 Incubation
<300> PUBLICATION INFORMATION:
<301> AUTHORS: Kridel, Steven J
      Chen, Emily
      Kotra, Lakshmi P
      Howard, Eric W
      Mobashery, Shahriar
      Smith, Jeffrey W
<302> TITLE: Substrate Hydrolysis By Matrix Metalloproteinase-9
<303> JOURNAL: The Journal of Biological Chemistry
<304> VOLUME: 276
<305> ISSUE: 23
<306> PAGES: 20572-20578
<307> DATE: 2001

<400> SEQUENCE: 29

Gly Pro Leu Arg Leu Ser Trp Gln
1               5

<210> SEQ ID NO 30
<211> LENGTH: 8
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-9 Incubation
<300> PUBLICATION INFORMATION:
<301> AUTHORS: Kridel, Steven J
      Chen, Emily
      Kotra, Lakshmi P
      Howard, Eric W
      Mobashery, Shahriar
      Smith, Jeffrey W
<302> TITLE: Substrate Hydrolysis By Matrix Metalloproteinase-9
<303> JOURNAL: The Journal of Biological Chemistry
<304> VOLUME: 276
<305> ISSUE: 23
<306> PAGES: 20572-20578
<307> DATE: 2001

<400> SEQUENCE: 30

Gly Pro Arg Ala Val Ser Thr Gln
1               5

<210> SEQ ID NO 31
<211> LENGTH: 9
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-9 Incubation
<300> PUBLICATION INFORMATION:
<301> AUTHORS: Kridel, Steven J
      Chen, Emily
      Kotra, Lakshmi P
      Howard, Eric W
      Mobashery, Shahriar
      Smith, Jeffrey W
<302> TITLE: Substrate Hydrolysis By Matrix Metalloproteinase-9
```

<303> JOURNAL: The Journal of Biological Chemistry
<304> VOLUME: 276
<305> ISSUE: 23
<306> PAGES: 20572-20578
<307> DATE: 2001

<400> SEQUENCE: 31

Lys Gly Pro Arg Gln Ile Thr Ala Gln
1               5

<210> SEQ ID NO 32
<211> LENGTH: 8
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-9 Incubation
<300> PUBLICATION INFORMATION:
<301> AUTHORS: Kridel, Steven J
      Chen, Emily
      Kotra, Lakshmi P
      Howard, Eric W
      Mobashery, Shahriar
      Smith, Jeffrey W
<302> TITLE: Substrate Hydrolysis By Matrix Metalloproteinase-9
<303> JOURNAL: The Journal of Biological Chemistry
<304> VOLUME: 276
<305> ISSUE: 23
<306> PAGES: 20572-20578
<307> DATE: 2001

<400> SEQUENCE: 32

Ala Gly Ser Gly Leu Lys Ala Gln
1               5

<210> SEQ ID NO 33
<211> LENGTH: 8
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-9 Incubation
<300> PUBLICATION INFORMATION:
<301> AUTHORS: Kridel, Steven J
      Chen, Emily
      Kotra, Lakshmi P
      Howard, Eric W
      Mobashery, Shahriar
      Smith, Jeffrey W
<302> TITLE: Substrate Hydrolysis By Matrix Metalloproteinase-9
<303> JOURNAL: The Journal of Biological Chemistry
<304> VOLUME: 276
<305> ISSUE: 23
<306> PAGES: 20572-20578
<307> DATE: 2001

<400> SEQUENCE: 33

Gly Ala Met Gly Leu Lys Ser Gln
1               5

<210> SEQ ID NO 34
<211> LENGTH: 9
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-9 Incubation
<300> PUBLICATION INFORMATION:
<301> AUTHORS: Kridel, Steven J
      Chen, Emily
      Kotra, Lakshmi P
      Howard, Eric W
      Mobashery, Shahriar

```
                Smith, Jeffrey W
<302> TITLE: Substrate Hydrolysis By Matrix Metalloproteinase-9
<303> JOURNAL: The Journal of Biological Chemistry
<304> VOLUME: 276
<305> ISSUE: 23
<306> PAGES: 20572-20578
<307> DATE: 2001

<400> SEQUENCE: 34

Ala Arg Gly Arg Arg Leu Ile His His
1               5

<210> SEQ ID NO 35
<211> LENGTH: 9
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-9 Incubation
<300> PUBLICATION INFORMATION:
<301> AUTHORS: Kridel, Steven J
       Chen, Emily
       Kotra, Lakshmi P
       Howard, Eric W
       Mobashery, Shahriar
       Smith, Jeffrey W
<302> TITLE: Substrate Hydrolysis By Matrix Metalloproteinase-9
<303> JOURNAL: The Journal of Biological Chemistry
<304> VOLUME: 276
<305> ISSUE: 23
<306> PAGES: 20572-20578
<307> DATE: 2001

<400> SEQUENCE: 35

Gly Leu Ala Arg Asn Ile Thr Ala Gln
1               5

<210> SEQ ID NO 36
<211> LENGTH: 9
<212> TYPE: PRT
<213> ORGANISM: Artificial Sequence
<220> FEATURE:
<223> OTHER INFORMATION: Sequence Generated in a Random Peptide Hexamer
      Substrate Phage Library and Selected by MMP-9 Incubation
<300> PUBLICATION INFORMATION:
<301> AUTHORS: Kridel, Steven J
       Chen, Emily
       Kotra, Lakshmi P
       Howard, Eric W
       Mobashery, Shahriar
       Smith, Jeffrey W
<302> TITLE: Substrate Hydrolysis By Matrix Metalloproteinase-9
<303> JOURNAL: The Journal of Biological Chemistry
<304> VOLUME: 276
<305> ISSUE: 23
<306> PAGES: 20572-20578
<307> DATE: 2001

<400> SEQUENCE: 36

Phe Gly Ser Arg Tyr Leu Thr Ala Gln
1               5

<210> SEQ ID NO 37
<211> LENGTH: 12
<212> TYPE: PRT
<213> ORGANISM: Homo sapiens
<220> FEATURE:
<221> NAME/KEY: Leukocyte Elastase Inhibitor
<222> LOCATION: FROM 339 TO 350
<300> PUBLICATION INFORMATION:
<308> DATABASE ACCESSION NUMBER: UniProtKB P30740
<300> PUBLICATION INFORMATION:
<301> AUTHORS: Korkmaz, Brice
```

```
          Attucci, Sylvie
          Hazouard, Eric
          Ferrandi?re, Martine
          Jourdan, Marie Lise
          Brillard-Bourdet, Mich?le
          Juliano, Luiz
          Gauthier, Francis
<302> TITLE: Discriminating Between the Activities of Human Neutrophil
      Elastase and Proteinase 3 Using Serpin-Derived Fluorogenic
      Substrates
<303> JOURNAL: The Journal of Biological Chemistry
<304> VOLUME: 277
<305> ISSUE: 42
<306> PAGES: 39074-39081
<307> DATE: 2002

<400> SEQUENCE: 37

Gly Ile Ala Thr Phe Cys Met Leu Met Pro Glu Gln
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Protease Cleavage Sequence

<400> SEQUENCE: 38

Ala Ala Pro Val Leu Ser Ala Gln
1               5

<210> SEQ ID NO 39
<211> LENGTH: 9
<212> TYPE: PRT
<213> ORGANISM: Homo sapiens
<220> FEATURE:
<221> NAME/KEY: Plasminogen Activator Inhibitor 1
<222> LOCATION: FROM 371 TO 380
<220> FEATURE:
<223> OTHER INFORMATION: Minus 385Ile; 378Asp to Arg; 380Pro to Gln
<300> PUBLICATION INFORMATION:
<308> DATABASE ACCESSION NUMBER: UniProtKB P05121
<300> PUBLICATION INFORMATION:
<301> AUTHORS: Korkmaz, B
          Attucci, S
          Epinette, C
          Pitois, E
          Jourdan, ML
          Juliano, L
          Gauthier, F
<302> TITLE: Measurement of Neutrophil Elastase, Proteinase 3, and
      Cathepsin G Activities Using Intramolecularly Quenched
      Fluorogenic Substrates
<303> JOURNAL: Methods in Molecular Biology
<304> VOLUME: 844
<306> PAGES: 125-138
<307> DATE: 2012

<400> SEQUENCE: 39

Ala Pro Glu Glu Ile Met Arg Arg Gln
1               5

<210> SEQ ID NO 40
<211> LENGTH: 8
<212> TYPE: PRT
<213> ORGANISM: Homo sapiens
<220> FEATURE:
<221> NAME/KEY: Stromal Cell-Derived Factor-1?
<222> LOCATION: FROM 21 TO 28
<300> PUBLICATION INFORMATION:
<308> DATABASE ACCESSION NUMBER: UniProtKB P48061
<300> PUBLICATION INFORMATION:
<301> AUTHORS: Korkmaz, Brice
```

```
            Horwitz, Marshall S
            Jenne, Dieter E
            Gauthier, Francis
<302> TITLE: Neutrophil Elastase, Proteinase 3, and Cathepsin G as
      Therapeutic Targets in Human Diseases
<303> JOURNAL: Pharmacological Reviews
<304> VOLUME: 62
<305> ISSUE: 4
<306> PAGES: 726-759
<307> DATE: 2010

<400> SEQUENCE: 40

Gly Lys Pro Val Ser Leu Ser Tyr
1               5

<210> SEQ ID NO 41
<211> LENGTH: 9
<212> TYPE: PRT
<213> ORGANISM: Homo sapiens
<220> FEATURE:
<221> NAME/KEY: Plasminogen Activator Inhibitor 1
<222> LOCATION: FROM 371 TO 380
<220> FEATURE:
<223> OTHER INFORMATION: Minus 385Ile; 380Pro to Gln
<300> PUBLICATION INFORMATION:
<308> DATABASE ACCESSION NUMBER: UniProtKB P05121
<300> PUBLICATION INFORMATION:
<301> AUTHORS: Korkmaz, Brice
            Attucci, Sylvie
            Hazouard, Eric
            Ferrandi?re, Martine
            Jourdan, Marie Lise
            Brillard-Bourdet, Mich?le
            Juliano, Luiz
            Gauthier, Francis
<302> TITLE: Discriminating Between the Activities of Human Neutrophil
      Elastase and Proteinase 3 Using Serpin-Derived Fluorogenic
      Substrates
<303> JOURNAL: The Journal of Biological Chemistry
<304> VOLUME: 277
<305> ISSUE: 42
<306> PAGES: 39074-39081
<307> DATE: 2002

<400> SEQUENCE: 41

Ala Pro Glu Glu Ile Met Asp Arg Gln
1               5

<210> SEQ ID NO 42
<211> LENGTH: 8
<212> TYPE: PRT
<213> ORGANISM: Homo sapiens
<220> FEATURE:
<221> NAME/KEY: Matrix Metalloproteinase-9
<222> LOCATION: FROM 54 TO 61
<300> PUBLICATION INFORMATION:
<308> DATABASE ACCESSION NUMBER: UniProtKB P14780
<300> PUBLICATION INFORMATION:
<301> AUTHORS: Jackson, Patricia L
            Xu, Xin
            Wilson, Landon
            Weathington, Nathaniel M
            Clancy, John Paul
            Blalock, James Edwin
            Gaggar, Amit
<302> TITLE: Human Neutrophil Elastase-Mediated Cleavage Sites of MMP-9
      and TIMP-1: Implications to Cystic Fibrosis Proteolytic
      Dysfunction
<303> JOURNAL: Molecular Medicine
<304> VOLUME: 16
<305> ISSUE: 5-6
<306> PAGES: 159-166
<307> DATE: 2010

<400> SEQUENCE: 42
```

Tyr Thr Arg Val Ala Glu Met Arg
1               5

<210> SEQ ID NO 43
<211> LENGTH: 8
<212> TYPE: PRT
<213> ORGANISM: Homo sapiens
<220> FEATURE:
<221> NAME/KEY: Matrix Metalloproteinase-9
<222> LOCATION: FROM 55 TO 62
<300> PUBLICATION INFORMATION:
<308> DATABASE ACCESSION NUMBER: UniProtKB P14780
<300> PUBLICATION INFORMATION:
<301> AUTHORS: Jackson, Patricia L
       Xu, Xin
       Wilson, Landon
       Weathington, Nathaniel M
       Clancy, John Paul
       Blalock, James Edwin
       Gaggar, Amit
<302> TITLE: Human Neutrophil Elastase-Mediated Cleavage Sites of MMP-9
       and TIMP-1: Implications to Cystic Fibrosis Proteolytic
       Dysfunction
<303> JOURNAL: Molecular Medicine
<304> VOLUME: 16
<305> ISSUE: 5-6
<306> PAGES: 159-166
<307> DATE: 2010

<400> SEQUENCE: 43

Thr Arg Val Ala Glu Met Arg Gly
1               5

<210> SEQ ID NO 44
<211> LENGTH: 8
<212> TYPE: PRT
<213> ORGANISM: Homo sapiens
<220> FEATURE:
<221> NAME/KEY: Metalloproteinase Inhibitor 1
<222> LOCATION: FROM 89 TO 96
<300> PUBLICATION INFORMATION:
<308> DATABASE ACCESSION NUMBER: UniProtKB P01033
<300> PUBLICATION INFORMATION:
<301> AUTHORS: Jackson, Patricia L
       Xu, Xin
       Wilson, Landon
       Weathington, Nathaniel M
       Clancy, John Paul
       Blalock, James Edwin
       Gaggar, Amit
<302> TITLE: Human Neutrophil Elastase-Mediated Cleavage Sites of MMP-9
       and TIMP-1: Implications to Cystic Fibrosis Proteolytic
       Dysfunction
<303> JOURNAL: Molecular Medicine
<304> VOLUME: 16
<305> ISSUE: 5-6
<306> PAGES: 159-166
<307> DATE: 2010

<400> SEQUENCE: 44

Met Glu Ser Val Cys Gly Tyr Phe
1               5

<210> SEQ ID NO 45
<211> LENGTH: 8
<212> TYPE: PRT
<213> ORGANISM: Artificial Sequence
<220> FEATURE:
<223> OTHER INFORMATION: Human Neutrophil Elastase Cleavage Sequence
<220> FEATURE:
<221> NAME/KEY: misc_feature
<222> LOCATION: (1)..(1)
<223> OTHER INFORMATION: Xaa is 6-Benzyl-Norleucine (Nle[O-Bzl])

```
<220> FEATURE:
<221> NAME/KEY: misc_feature
<222> LOCATION: (2)..(2)
<223> OTHER INFORMATION: Xaa is Methionine Dioxide (Met[O2])
<220> FEATURE:
<221> NAME/KEY: misc_feature
<222> LOCATION: (3)..(3)
<223> OTHER INFORMATION: Xaa is Octahydro-1H-Indole-2-Carboxylic Acid
      (Oic)
<220> FEATURE:
<221> NAME/KEY: misc_feature
<222> LOCATION: (4)..(4)
<223> OTHER INFORMATION: Xaa is Aminobutyric Acid (Abu)
<300> PUBLICATION INFORMATION:
<301> AUTHORS: Kasperkiewicz, Paulina
      Poreba, Marcin
      Snipas, Scott J
      Parker, Heather
      Winterbourn, Christine C
      Salvesen, Guy S
      Drag, Marcin
<302> TITLE: Design of Ultrasensitive Probes For Human Neutrophil
      Elastase Through Hybrid Combinatorial Substrate Library
      Profiling
<303> JOURNAL: Proceedings of the National Academy of Sciences of the
      United States of America
<304> VOLUME: 111
<305> ISSUE: 7
<306> PAGES: 2518-2523
<307> DATE: 2014

<400> SEQUENCE: 45

Xaa Xaa Xaa Xaa Leu Ser Ala Gln
1               5

<210> SEQ ID NO 46
<211> LENGTH: 20
<212> TYPE: PRT
<213> ORGANISM: Artificial Sequence
<220> FEATURE:
<223> OTHER INFORMATION: Composition of SEQ ID NO 3 (Peptide From Human
      Collagen Type I) and SEQ ID NO 37 (Peptide from Leukocyte Elastase
      Inhibitor)

<400> SEQUENCE: 46

Gly Pro Gln Gly Ile Phe Gly Gln Gly Ile Ala Thr Phe Cys Met Leu
1               5                   10                  15

Met Pro Glu Gln
            20

<210> SEQ ID NO 47
<211> LENGTH: 16
<212> TYPE: PRT
<213> ORGANISM: Artificial Sequence
<220> FEATURE:
<223> OTHER INFORMATION: Composition of SEQ ID NO 3 (Peptide From Human
      Collagen Type I) and SEQ ID NO 38

<400> SEQUENCE: 47

Gly Pro Gln Gly Ile Phe Gly Gln Ala Ala Pro Val Leu Ser Ala Gln
1               5                   10                  15

<210> SEQ ID NO 48
<211> LENGTH: 19
<212> TYPE: PRT
<213> ORGANISM: Homo sapiens
<220> FEATURE:
<221> NAME/KEY: Apolipoprotein E
<222> LOCATION: FROM 150 TO 167
<220> FEATURE:
<221> NAME/KEY: misc_feature
<223> OTHER INFORMATION: With N-Terminal Cysteine for Attachment to
```

```
      Electrode Surface
<300> PUBLICATION INFORMATION:
<308> DATABASE ACCESSION NUMBER: UniProtKB P02649
<300> PUBLICATION INFORMATION:
<301> AUTHORS: Rall, Stanley C
      Weisgraber, Karl H
      Mahley, Robert W
<302> TITLE: Human Apolipoprotein E: The Complete Amino Acid Sequence
<303> JOURNAL: The Journal of Biological Chemistry
<304> VOLUME: 257
<305> ISSUE: 8
<306> PAGES: 4171-4178
<307> DATE: 1982

<400> SEQUENCE: 48

Cys Glu Glu Leu Arg Val Arg Leu Ala Ser His Leu Arg Lys Leu Arg
1               5                   10                  15

Lys Arg Leu

<210> SEQ ID NO 49
<211> LENGTH: 9
<212> TYPE: PRT
<213> ORGANISM: Artificial Sequence
<220> FEATURE:
<223> OTHER INFORMATION: With N-Terminal Cysteine for Attachment to
      Electrode Surface

<400> SEQUENCE: 49

Cys Val Leu Val Leu Val Leu Val Leu
1               5

<210> SEQ ID NO 50
<211> LENGTH: 10
<212> TYPE: PRT
<213> ORGANISM: Artificial Sequence
<220> FEATURE:
<223> OTHER INFORMATION: With C-Terminal Cysteine for Attachment to
      Electrode Surface

<400> SEQUENCE: 50

Asp Asp Ala Ala Asp Asp Ser Ala Asp Cys
1               5                   10

<210> SEQ ID NO 51
<211> LENGTH: 27
<212> TYPE: PRT
<213> ORGANISM: Artificial Sequence
<220> FEATURE:
<223> OTHER INFORMATION: Composition of SEQ ID NO 48 (Peptide From Human
      Apolipoprotein E) and SEQ ID NO 3 (Peptide From Human
      Collagen Type I)

<400> SEQUENCE: 51

Cys Glu Glu Leu Arg Val Arg Leu Ala Ser His Leu Arg Lys Leu Arg
1               5                   10                  15

Lys Arg Leu Gly Pro Gln Gly Ile Phe Gly Gln
            20                  25

<210> SEQ ID NO 52
<211> LENGTH: 21
<212> TYPE: PRT
<213> ORGANISM: Artificial Sequence
<220> FEATURE:
<223> OTHER INFORMATION: Composition of SEQ ID NO 49 and SEQ ID NO 37
      (Peptide From Human Leukocyte Elastase Inhibitor)

<400> SEQUENCE: 52

Cys Val Leu Val Leu Val Leu Val Leu Gly Ile Ala Thr Phe Cys Met
```

```
1               5                  10                 15
Leu Met Pro Glu Gln
            20

<210> SEQ ID NO 53
<211> LENGTH: 42
<212> TYPE: PRT
<213> ORGANISM: Homo sapiens
<220> FEATURE:
<223> OTHER INFORMATION: Composition of SEQ ID NO 48 (Peptide From Human
      Apolipoprotein E), SEQ ID NO 3 (Peptide From Human
      Collagen Type I) and an aptamer recognition sequence from
      Human Histone H4
<220> FEATURE:
<221> NAME/KEY: Histone H4
<222> LOCATION: FROM 7 TO 21
<220> FEATURE:
<221> NAME/KEY: modified amino acid
<222> LOCATION: (38)..(38)
<223> OTHER INFORMATION: Lys is Acetylated
<300> PUBLICATION INFORMATION:
<308> DATABASE ACCESSION NUMBER: UniProtKB P62805
<300> PUBLICATION INFORMATION:
<301> AUTHORS: Williams, Berea AR
      Lin, Liyun
      Lindsay, Stuart M
      Chaput, John C
<302> TITLE: Evolution of a Histone H4-K16 Acetyl-Specific DNA Aptamer
<303> JOURNAL: The Journal of the American Chemical Society
<304> VOLUME: 131
<305> ISSUE: 18
<306> PAGES: 6330-6331
<307> DATE: 2009

<400> SEQUENCE: 53

Cys Glu Glu Leu Arg Val Arg Leu Ala Ser His Leu Arg Lys Leu Arg
1               5                  10                 15

Lys Arg Leu Gly Pro Gln Gly Ile Phe Gly Gln Gly Gly Lys Gly
            20                  25                 30

Leu Gly Lys Gly Gly Ala Lys Arg His Arg Lys
        35                  40

<210> SEQ ID NO 54
<211> LENGTH: 13
<212> TYPE: DNA
<213> ORGANISM: Artificial Sequence
<220> FEATURE:
<223> OTHER INFORMATION: Synthetic: Used For Conjugation to a Peptide
      Sequence

<400> SEQUENCE: 54
ccatctccac tgc                                                      13

<210> SEQ ID NO 55
<211> LENGTH: 28
<212> TYPE: PRT
<213> ORGANISM: Artificial Sequence
<220> FEATURE:
<223> OTHER INFORMATION: Synthetic SEQ ID NO 51
<220> FEATURE:
<221> NAME/KEY: modified amino acid
<222> LOCATION: (28)..(28)
<223> OTHER INFORMATION: Xaa is Azidolysine (Lys[N3])
<220> FEATURE:
<223> OTHER INFORMATION: A nucleotide sequence (SEQ ID NO 62) is
      attached to the Azidolysine at the carboxy-terminus

<400> SEQUENCE: 55

Cys Glu Glu Leu Arg Val Arg Leu Ala Ser His Leu Arg Lys Leu Arg
1               5                  10                 15
```

Lys Arg Leu Gly Pro Gln Gly Ile Phe Gly Gln Xaa
           20                  25

<210> SEQ ID NO 56
<211> LENGTH: 34
<212> TYPE: DNA
<213> ORGANISM: Artificial Sequence
<220> FEATURE:
<223> OTHER INFORMATION: Signaling Oligonucleotide
<220> FEATURE:
<221> NAME/KEY: misc_feature
<222> LOCATION: (1)..(1)
<223> OTHER INFORMATION: n is 3 Prime-Methylene Blue Ethyl Cytosine
<220> FEATURE:
<221> NAME/KEY: misc_feature
<222> LOCATION: (34)..(34)
<223> OTHER INFORMATION: n is 5 Prime-Hexyl 1-Hexyl Disulfyl Cytosine

<400> SEQUENCE: 56
nccaacctgt gttgtgggtt gcagtggaga tggn                              34

<210> SEQ ID NO 57
<211> LENGTH: 59
<212> TYPE: DNA
<213> ORGANISM: Artificial Sequence
<220> FEATURE:
<223> OTHER INFORMATION: Signaling Aptamer
<220> FEATURE:
<221> NAME/KEY: misc_feature
<222> LOCATION: (1)..(1)
<223> OTHER INFORMATION: n is 5 Prime-Methylene Blue Ethyl Cytosine
<220> FEATURE:
<221> NAME/KEY: misc_feature
<222> LOCATION: (59)..(59)
<223> OTHER INFORMATION: n is 3 Prime-Hexyl 1-Hexyl Disulfyl Cytosine

<400> SEQUENCE: 57
ngtaagttaa ttggacttgg tcgtgtgcgg cacagcgatt tgggtgttgt gtccaaccn   59

<210> SEQ ID NO 58
<211> LENGTH: 28
<212> TYPE: DNA
<213> ORGANISM: Artificial Sequence
<220> FEATURE:
<223> OTHER INFORMATION: Signaling Oligonucleotide
<220> FEATURE:
<221> NAME/KEY: misc_feature
<222> LOCATION: (1)..(1)
<223> OTHER INFORMATION: n is 5 Prime-Sulfhydryl Hexanyl Cytosine
<220> FEATURE:
<221> NAME/KEY: misc_feature
<222> LOCATION: (28)..(28)
<223> OTHER INFORMATION: n is 3 Prime-Methylene Blue Ethyl Guanine

<400> SEQUENCE: 58
ncatctccac tcgttttcg tgcttctn                                      28

<210> SEQ ID NO 59
<211> LENGTH: 28
<212> TYPE: DNA
<213> ORGANISM: Artificial Sequence
<220> FEATURE:
<223> OTHER INFORMATION: Signaling Oligonucleotide
<220> FEATURE:
<221> NAME/KEY: misc_feature
<222> LOCATION: (1)..(1)
<223> OTHER INFORMATION: n is 5 Prime-Sulfhydryl Hexanyl Cytosine
<220> FEATURE:
<221> NAME/KEY: misc_feature
<222> LOCATION: (28)..(28)
<223> OTHER INFORMATION: n is 3 Prime-Methylene Blue Ethyl Cytosine

<400> SEQUENCE: 59
ngtgcttctg ctgtttttcc atctccan        28

<210> SEQ ID NO 60
<211> LENGTH: 8
<212> TYPE: PRT
<213> ORGANISM: Artificial Sequence
<220> FEATURE:
<223> OTHER INFORMATION: Inverted Synthetic PEP ID NO 3
<220> FEATURE:
<221> NAME/KEY: modified amino acid
<222> LOCATION: (8)..(8)
<223> OTHER INFORMATION: Xaa is Dimethyloxytrityl-Glycine
<220> FEATURE:
<223> OTHER INFORMATION: A nucleotide sequence (SEQ ID NO 63) is
      attached via its 3 Prime-guanine-triazole to the carboxy-terminal
      glutamine residue 1
<220> FEATURE:
<223> OTHER INFORMATION: A nucleotide sequence (SEQ ID NO 64) is
      attached via its 5 Prime-guanine to the amino-terminal
      dimethyloxytrityl-glycine residue 8

<400> SEQUENCE: 60

Gln Gly Phe Ile Gly Gln Pro Xaa
1               5

<210> SEQ ID NO 61
<211> LENGTH: 8
<212> TYPE: PRT
<213> ORGANISM: Artificial Sequence
<220> FEATURE:
<223> OTHER INFORMATION: Inverted Synthetic PEP ID NO 38
<220> FEATURE:
<221> NAME/KEY: modified amino acid
<222> LOCATION: (8)..(8)
<223> OTHER INFORMATION: Xaa is Dimethyloxytrityl-Alanine
<220> FEATURE:
<223> OTHER INFORMATION: A nucleotide sequence (SEQ ID NO 65) is
      attached via its 3 Prime-guanine-triazole to the carboxy-terminal
      glutamine residue 1
<220> FEATURE:
<223> OTHER INFORMATION: A nucleotide sequence (SEQ ID NO 66) is
      attached via its 5 Prime-adenine to the amino-terminal
      dimethyloxytrityl-alanine residue 8

<400> SEQUENCE: 61

Gln Ala Ser Leu Val Pro Ala Xaa
1               5

<210> SEQ ID NO 62
<211> LENGTH: 13
<212> TYPE: DNA
<213> ORGANISM: Artificial Sequence
<220> FEATURE:
<223> OTHER INFORMATION: The 5 Prime end of this linker nucleotide
      sequence is attached to the azidolysine residue at the carboxy-
      terminus of SEQ ID NO 55
<220> FEATURE:
<221> NAME/KEY: misc_feature
<222> LOCATION: (1)..(1)
<223> OTHER INFORMATION: n is 5 Prime-hexynyl-cytosine

<400> SEQUENCE: 62
ncatctccac tgc        13

<210> SEQ ID NO 63
<211> LENGTH: 11
<212> TYPE: DNA
<213> ORGANISM: Artificial Sequence
<220> FEATURE:

-continued

```
<223> OTHER INFORMATION: The 3 Prime-guanine-triazole base of this
      linker nucleotide sequence is attached to the carboxy-terminal
      glutamine residue 1 of SEQ ID NO 60
<220> FEATURE:
<221> NAME/KEY: misc_feature
<222> LOCATION: (11)..(11)
<223> OTHER INFORMATION: n is Guanine-triazole

<400> SEQUENCE: 63
tcagaagcac n                                                          11

<210> SEQ ID NO 64
<211> LENGTH: 12
<212> TYPE: DNA
<213> ORGANISM: Artificial Sequence
<220> FEATURE:
<223> OTHER INFORMATION: The first 5 Prime-guanine base of this linker
      nucleotide sequence is attached to the amino-terminal
      dimethyloxytrityl-glycine residue 8 of SEQ ID NO 60
<220> FEATURE:
<221> NAME/KEY: misc_feature
<222> LOCATION: (12)..(12)
<223> OTHER INFORMATION: n is 3 Prime-Sulfhydryl Hexanyl Guanine

<400> SEQUENCE: 64
gagtggagat gn                                                         12

<210> SEQ ID NO 65
<211> LENGTH: 11
<212> TYPE: DNA
<213> ORGANISM: Artificial Sequence
<220> FEATURE:
<223> OTHER INFORMATION: The 3 Prime guanine-triazole base of this
      linker nucleotide sequence is attached to the carboxy-terminal
      glutamine residue 1 of SEQ ID NO 61
<220> FEATURE:
<221> NAME/KEY: misc_feature
<222> LOCATION: (11)..(11)
<223> OTHER INFORMATION: n is Guanine-triazole

<400> SEQUENCE: 65
tgtggagatg n                                                          11

<210> SEQ ID NO 66
<211> LENGTH: 12
<212> TYPE: DNA
<213> ORGANISM: Artificial Sequence
<220> FEATURE:
<223> OTHER INFORMATION: The first 5 Prime-adenine base of this linker
      nucleotide sequence is attached to the amino-terminal
      dimethyloxytrityl-alanine residue 8 of SEQ ID NO 61
<220> FEATURE:
<221> NAME/KEY: misc_feature
<222> LOCATION: (12)..(12)
<223> OTHER INFORMATION: n is 3 Prime-Sulfhydryl Hexanyl Guanine

<400> SEQUENCE: 66
agcagaagca cn                                                         12
```